United States Patent [19]

Hidaka et al.

[11] 4,456,757
[45] Jun. 26, 1984

[54] ISOQUINOLINESULFONYL DERIVATIVES AND PROCESS FOR THE PREPARATION THEREOF

[75] Inventors: Hiroyoshi Hidaka, 799-25, Kannonji-cho, Tsu-shi, Mie-ken; Takanori Sone, Nobeoka; Yasuharu Sasaki, Nobeoka; Taisuke Sugihara, Nobeoka, all of Japan

[73] Assignees: Asahi Kasei Kogyo Kabushiki Kaisha, Osaka; Hiroyoshi Hidaka, Tsu, both of Japan

[21] Appl. No.: 357,770

[22] Filed: Mar. 12, 1982

[30] Foreign Application Priority Data

Mar. 20, 1981 [JP] Japan .................................. 56-39550
Jun. 1, 1981 [JP] Japan .................................. 56-82559
Jan. 12, 1982 [JP] Japan .................................. 57-2229
Jan. 14, 1982 [JP] Japan .................................. 57-3291

[51] Int. Cl.$^3$ .................. C07D 217/02; C07D 401/12; C07D 413/12; A61K 31/47
[52] U.S. Cl. .................................. 546/139; 424/248.5; 424/250; 424/258; 544/128; 544/363
[58] Field of Search .................. 260/244.4; 546/139, 546/149

[56] References Cited

U.S. PATENT DOCUMENTS 4,315,935 * 2/1982 Ali .......................................... 546/139
4,317,826 3/1982 Gleason .............................. 546/139

Primary Examiner—Mary C. Lee
Assistant Examiner—J. H. Turnipseed
Attorney, Agent, or Firm—Finnegan, Henderson, Farabow, Garrett & Dunner

[57] ABSTRACT

A 5-isoquinolinesulfonyl derivative of Formula (I):

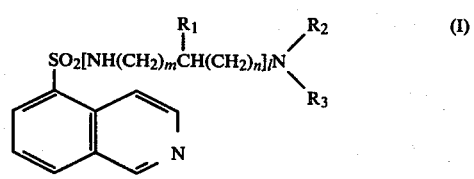

wherein l is zero or one;
m and n each is an integer of one to nine;
m+n is an integer of at least one;
$R_1$ is a hydrogen atom, a $C_{1-10}$ alkyl group, a $C_{5-6}$ cycloalkyl group or an aryl group; or
$R_2$ and $R_3$ each is a hydrogen atom, a $C_{1-10}$ alkyl group, a $C_{5-6}$ cycloalkyl group, an aryl group or an aralkyl group;
$R_2$ and $R_3$ are $C_{1-6}$ alkylene groups and linked directly or through an oxygen atom to form a 5- to 7-membered heterocyclic ring with the adjacent nitrogen atom; or
the

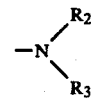

group is a

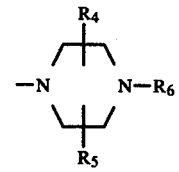

group wherein $R_4$ and $R_5$ each is a hydrogen atom, a $C_{1-10}$ alkyl group, an aryl group or an aralkyl group and $R_6$ is a hydrogen atom, a $C_{1-10}$ alkyl group, and aryl group, an aralkyl group, a benzoyl group, a cinnamyl group, a cinnamoyl group, a furoyl group or a

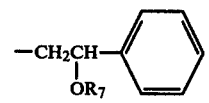

group wherein $R_7$ is a $C_{1-8}$ alkyl group;
and the pharmaceutically acceptable salt thereof; and a process for the preparation thereof. The compounds of this invention have a relaxatory action for vascular smooth muscle and are useful as a vasodilator and a hypotensor.

9 Claims, No Drawings

ISOQUINOLINESULFONYL DERIVATIVES AND PROCESS FOR THE PREPARATION THEREOF

BACKGROUND OF THE INVENTION

Field of the Invention

This invention relates to novel isoquinolinesulfonyl derivatives which possess a relaxatory action for vascular smooth muscle and are useful as a vasodilator and a hypotensor, and a process for the preparation thereof.

SUMMARY OF THE INVENTION

According to the present invention in one embodiment there is provided an isoquinoline derivative of Formula (I):

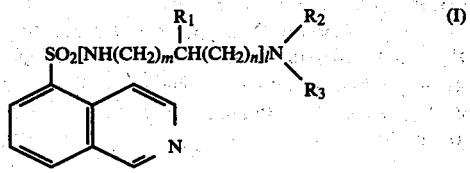

wherein l is zero or one;

m and n each is zero or an integer of one to nine;

m+n is an integer of at least one;

$R_1$ is a hydrogen atom, a $C_{1-10}$ alkyl group, a $C_{5-6}$ cycloalkyl group or an aryl group;

$R_2$ and $R_3$ each is a hydrogen atom, a $C_{1-10}$ alkyl group, a $C_{5-6}$ cycloalkyl group, an aryl group or an aralkyl group;

$R_2$ and $R_3$ may be $C_{1-6}$ alkylene groups linked directly or through an oxygen atom to form a 5- to 7-membered heterocyclic ring with the adjacent nitrogen atom; or the

group is a

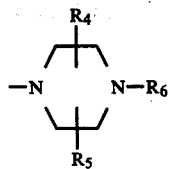

group wherein $R_4$ and $R_5$ each is a hydrogen atom, a $C_{1-10}$ alkyl group, an aryl group or an aralkyl group and $R_6$ is a hydrogen atom, a $C_{1-10}$ alkyl group, an aryl group, an aralkyl group, a benzoyl group, a cinnamyl group, a cinnamoyl group, a furoyl group or a

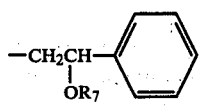

group wherein $R_7$ is a $C_{1-8}$ alkyl group;

or the pharmaceutically acceptable acid addition salt thereof.

The present invention in another embodiment provides a process of preparing the above described isoquinolinesulfonyl derivative.

DETAILED DESCRIPTION OF THE INVENTION

Exemplary $R_1$ groups in Formula (I) include a hydrogen atom; $C_{1-10}$ alkyl groups, preferably $C_{1-6}$ alkyl groups, such as methyl, ethyl, n-propyl, isopropyl, n-butyl, isobutyl, sec-butyl, tert-butyl, n-pentyl, n-hexyl, n-heptyl, n-octyl, n-nonyl and decyl; $C_{5-6}$ cycloalkyl groups such as cyclopentyl and cyclohexyl; and aryl groups such as phenyl. The $R_2$ and $R_3$ groups in Formula (I) may be the same or different and exemplary $R_2$ and $R_3$ groups include a hydrogen atom; $C_{1-10}$ alkyl groups, preferably $C_{1-8}$ alkyl groups such as methyl, ethyl, n-propyl, isopropyl, n-butyl, isobutyl, sec-butyl, tert-butyl, n-pentyl, isopentyl, n-hexyl, n-heptyl, n-octyl, n-nonyl and n-decyl; $C_{5-6}$ cycloalkyl groups such as cyclopentyl and cyclohexyl; aryl groups such as phenyl; and aralkyl groups such as benzyl. Exemplary 5- to 7-membered heterocyclic rings formed by linking $R_2$ and $R_3$ directly or through an oxygen atom together with the adjacent nitrogen atom include 1-pyrrolidinyl, piperidino, homopiperidino and morpholino groups. Preferred

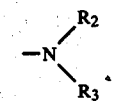

groups include amino, methylamino, ethylamino, n-propylamino, isopropylamino, n-butylamino, isobutylamino, n-hexylamino, cyclohexylamino, dimethylamino, diethylamino, di-n-butylamino, N-methyl-N-cyclopentylamino, N-methyl-N-cyclohexylamino, N-methyl-N-phenylamino, N-methyl-N-benzylamino, N-ethyl-N-benzylamino, N-isopropyl-N-benzylamino, 1-pyrrolidinyl, piperidino, homopiperidino and morpholino groups. The

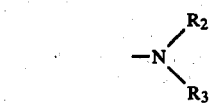

group may also be a

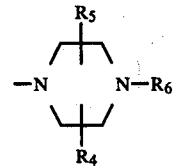

group. The $R_2$ and $R_3$ groups may be the same or different and exemplary $R_4$ and $R_5$ groups include a hydrogen atom; $C_{1-10}$ alkyl groups, preferably $C_{1-6}$ alkyl groups, such as methyl, ethyl, n-propyl, isopropyl, n-butyl, isobutyl, n-pentyl, isopentyl, n-hexyl, n-heptyl, n-octyl, n-nonyl, and n-decyl; $C_{5-6}$ cycloalkyl groups such as cyclopentyl and cyclohexyl; aryl group such as phenyl; and aralkyl groups such as benzyl, α-phenethyl and β-phenethyl. Exemplary $R_6$ groups include a hydrogen atom; $C_{1-10}$ alkyl groups, preferably $C_{1-6}$ alkyl groups, such as methyl, ethyl, n-propyl, isopropyl, n-butyl, isobutyl, n-pentyl, isopentyl, n-hexyl, n-heptyl, n-octyl, n-nonyl and n-decyl; aryl groups such as phenyl; aralkyl groups such as benzyl, α-phenethyl and β-phenethyl; a benzoyl group; a cinnamyl group; a cinnamoyl group; a furoyl group; a

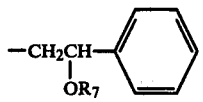

group wherein $R_7$ is a $C_{1-8}$ alkyl group, preferably a $C_{1-4}$ alkyl group, such as methyl, ethyl, n-propyl, isopropyl, n-butyl, isobutyl, n-pentyl, n-hexyl, n-heptyl and n-octyl groups. Preferred

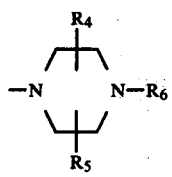

groups include piperazino, 2-methylpiperazino, 2-ethylpiperazino, 3-ethylpiperazino, 3-isopropylpiperazino, 3-isobutylpiperazino, 2-phenylpiperazino, 3-phenylpiperazino, 3-benzylpiperazino, 2,3-dimethylpiperazino, 2,5-dimethylpiperazino, 3,5-dimethylpiperazino, 2,6-dimethylpiperazino, 2-methyl-5-ethylpiperazino, 2-methyl-5-n-propylpiperazino, 2-methyl-5-isopropylpiperazino, 2-methyl-5-isobutylpiperazino, 2-methyl-5-phenylpiperazino, 2-methyl-5-benzylpiperazino, 2,5-diethylpiperazino, 2-ethyl-5-n-butylpiperazino, 4-methylpiperazino, 4-ethylpiperazino, 4-n-propylpiperazino, 4-isobutylpiperazino, 4-n-hexylpiperazino, 4-phenylpiperazino, 4-benzylpiperazino, 4-phenethylpiperazino, 4-benzoylpiperazino, 4-cinnamylpiperazino, 4-cinnamoylpiperazino, 4-furoylpiperazino, 4-(2-methoxy-2-phenethyl)piperazino and 4-(2-ethoxy-2-phenethyl)piperazino groups.

Preferred embodiments are as follows:
(a) A compound of Formula (XIII)

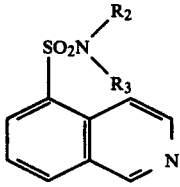

(XIII)

wherein
$R_2$ and $R_3$ each is a hydrogen atom, a $C_{1-8}$ alkyl group, a phenyl group or a benzyl group, and when one of $R_2$ and $R_3$ is a hydrogen atom, the other is not a hydrogen atom; or
$R_2$ and $R_3$ are $C_{1-6}$ alkylene groups linked directly or through an oxygen atom to form a 5- to 7-membered heterocyclic ring together with the adjacent nitrogen atom; or
the

group is a

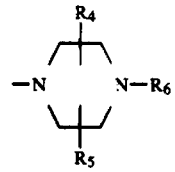

group wherein $R_4$ and $R_5$ each is a hydrogen atom, a $C_{1-6}$ alkyl group, a phenyl group or a benzyl group and $R_6$ is a hydrogen atom, a $C_{1-6}$ alkyl group, a phenyl group, a benzyl group, a phenethyl group, a benzoyl group, a cinnamyl group, a cinnamoyl group, a furoyl group or a

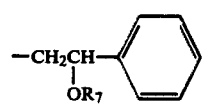

group wherein $R_7$ is a $C_{1-4}$ alkyl group;
and pharmaceutically acceptable acid addition salts thereof, i.e., a compound of Formula (I) wherein l is zero.
(b) The compound of (a), wherein $R_2$ is a hydrogen atom or a $C_{1-6}$ alkyl group and $R_3$ is a $C_{1-6}$ alkyl group.
(c) The compound of (a), wherein the

group is a 1-pyrrolidinyl group, a piperidino group or a morpholino group.
(d) The compound of (a), wherein the

group is a

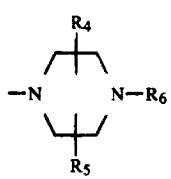

group wherein $R_6$ is a hydrogen atom and $R_4$ and $R_5$ each is a hydrogen atom, a $C_{1-6}$ alkyl group, a phenyl group or a benzyl group.
(e) The compound of (d), wherein $R_6$, $R_4$ and $R_5$ are hydrogen atoms.

(f) The compound of (d), wherein $R_4$ is a hydrogen atom or a $C_{1-6}$ alkyl group and $R_5$ is a $C_{1-6}$ alkyl group, a phenyl group or a benzyl group.

(g) The compound of (a), wherein the

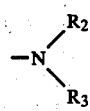

group is a

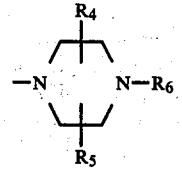

group wherein $R_4$ and $R_5$ are hydrogen atoms and $R_6$ is a $C_{1-6}$ alkyl group, a phenyl group, a benzyl group, a phenethyl group, a benzoyl group, a cinnamyl group, a cinnamoyl group, a furoyl group or a

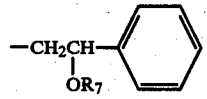

group wherein $R_7$ is a $C_{1-4}$ alkyl group.

(h) The compound of (g), wherein $R_6$ is a $C_{1-6}$ alkyl group.

(i) The compound of (g), wherein $R_6$ is a phenyl group, a benzyl group, a phenethyl group, a benzoyl group, a cinnamyl group, a cinnamoyl group or a furoyl group.

(j) The compound of (g), wherein $R_6$ is a

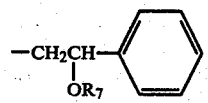

group wherein $R_7$ is a $C_{1-4}$ alkyl group.

(k) A compound of Formula (XIV):

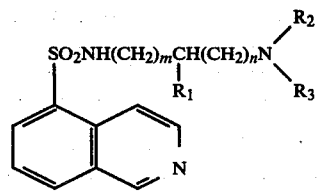

wherein
m and n each is zero or an integer of one to nine;
m+n is an integer of one to nine;
$R_1$ is a hydrogen atom, a $C_{1-6}$ alkyl group or a phenyl group;
$R_2$ and $R_3$ each is a hydrogen atom, a $C_{1-8}$ alkyl group, a $C_{5-6}$ cycloalkyl group, a phenyl group or a benzyl group; or
$R_2$ and $R_3$ are $C_{1-6}$ alkylene groups linked directly or through an oxygen atom to form a 5- to 7-membered heterocyclic ring together with the adjacent nitrogen atom; or
the

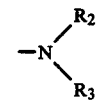

group is a

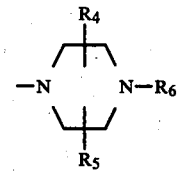

group wherein $R_4$ and $R_5$ each is a hydrogen atom, a $C_{1-6}$ alkyl group, a phenyl group or a benzyl group and $R_6$ is a hydrogen atom, a $C_{1-6}$ alkyl group, a phenyl group, a benzyl group, a phenethyl group, a benzoyl group, a cinnamyl group, a cinnamoyl group, a furoyl group or a

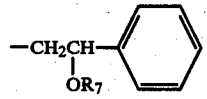

group wherein $R_7$ is a $C_{1-4}$ alkyl group;
or the pharmaceutically acceptable acid addition salts thereof, i.e., a compound of Formula (I), wherein l is one.

(l) The compound of (k), wherein m and n each is zero or an integer of one to nine, m+n is an integer of one to nine and $R_1$, $R_2$ and $R_3$ are hydrogen atoms.

(m) The compound of (k), wherein m and n each is zero or one, m+n is one, $R_2$ and $R_3$ are hydrogen atoms and $R_1$ is a $C_{1-6}$ alkyl group or a phenyl group.

(n) The compound of (k), wherein m and n each is zero or an integer of one to two, m+n is one or two, $R_1$ is a hydrogen atom, $R_2$ is a hydrogen atom or a $C_{1-4}$ alkyl group and $R_3$ is a $C_{1-6}$ alkyl group, a $C_{5-6}$ cycloalkyl group, a phenyl group or a benzyl group.

(o) The compound of (k), wherein m and n each is zero or an integer of one to two, m+n is one or two, $R_1$ is a hydrogen atom and $R_2$ and $R_3$ form together with the adjacent nitrogen atom a piperidino group or a morpholino group.

Exemplary isoquinolinesulfonyl derivatives of this invention include:

(1) N-(2-aminoethyl)-5-isoquinolinesulfonamide referred to as "Compound (1)";

(2) N-(3-aminopropyl)-5-isoquinolinesulfonamide referred to as "Compound (2)";

(3) N-(4-aminobutyl)-5-isoquinolinesulfonamide referred to as "Compound (3)";

(4) N-(6-aminohexyl)-5-isoquinolinesulfonamide referred to as "Compound (4)";

(5) N-(10-aminodecyl)-5-isoquinolinesulfonamide referred to as "Compound (5)";

(6) N-(2-amino-1-methylethyl)-5-isoquinolinesulfonamide referred to as "Compound (6)";

(7) N-(1-aminomethylpropyl)-5-isoquinolinesulfonamide referred to as "Compound (7)";

(8) N-(1-aminomethylpentyl)-5-isoquinolinesulfonamide referred to as "Compound (8)";
(9) N-(2-aminopropyl)-5-isoquinolinesulfonamide referred to as "Compound (9)";
(10) N-(2-aminobutyl)-5-isoquinolinesulfonamide referred to as "Compound (10)";
(11) N-(2-amino-3-methylbutyl)-5-isoquinolinesulfonamide referred to as "Compound (11)";
(12) N-(2-amino-1-phenylethyl)-5-isoquinolinesulfonamide referred to as "Compound (12)";
(13) N-(2-amino-2-phenylethyl)-5-isoquinolinesulfonamide referred to as "Compound (13)";
(14) N-(2-methylaminoethyl)-5-isoquinolinesulfonamide referred to as "Compound (14)";
(15) N-(2-ethylaminoethyl)-5-isoquinolinesulfonamide referred to as "Compound (15)";
(16) N-(2-isopropylaminoethyl)-5-isoquinolinesulfonamide referred to as "Compound (16)";
(17) N-(3-dimethylaminopropyl)-5-isoquinolinesulfonamide referred to as "Compound (17)";
(18) N-(3-diethylaminopropyl)-5-isoquinolinesulfonamide referred to as "Compound (18)";
(19) N-(3-di-n-butylaminopropyl)-5-isoquinolinesulfonamide referred to as "Compound (19)";
(20) N-(3-piperidinopropyl)-5-isoquinolinesulfonamide referred to as "Compound (20)";
(21) N-(3-morpholinopropyl)-5-isoquinolinesulfonamide referred to as "Compound (21)";
N-[3-(N-methyl-N-cyclohexylamino)propyl]-5-isoquinolinesulfonamide referred to as "Compound (22)";
(23) N-[3-(N-methyl-N-phenylamino)propyl]-5-isoquinolinesulfonamide referred to as "Compound (23)";
(24) N-[3-(N-methyl-N-benzylamino)propyl]-5-isoquinolinesulfonamide referred to as "Compound (24)";
(25) N-methyl-5-isoquinolinesulfonamide referred to as "Compound (25)";
(26) N-ethyl-5-isoquinolinesulfonamide referred to as "Compound (26)";
(27) N-n-Butyl-5-isoquinolinesulfonamide referred to as "Compound (27)";
(28) N-isobutyl-5-isoquinolinesulfonamide referred to as "Compound (28)";
(29) N,N-dimethyl-5-isoquinolinesulfonamide referred to as "Compound (29)";
(30) N,N-diethyl-5-isoquinolinesulfonamide referred to as "Compound (30)";
(31) N,N-di-n-butyl-5-isoquinolinesulfonamide referred to as "Compound (31)";
(32) 1-(5-isoquinolinesulfonyl)piperidine referred to as "Compound (32)";
(33) 4-(5-isoquinolinesulfonyl)pyrrolidine referred to as "Compound (33)";
(34) 1-(5-isoquinolinesulfonyl)morpholine referred to as "Compound (34)";
(35) 1-(5-isoquinolinesulfonyl)piperazine referred to as "Compound (35)";
(36) 1-(5-isoquinolinesulfonyl)-4-methylpiperazine referred to as "Compound (36)";
(37) 1-(5-isoquinolinesulfonyl)-3-methylpiperazine referred to as "Compound (37)";
(38) 1-(5-isoquinolinesulfonyl)-2-methylpiperazine referred to as "Compound (38)";
(39) 1-(5-isoquinolinesulfonyl)-3,5-dimethylpiperazine referred to as "Compound (39)";
(40) 1-(5-isoquinolinesulfonyl)-2,5-dimethylpiperazine referred to as "Compound (40)";
(41) 1-(5-isoquinolinesulfonyl)-2,3-dimethylpiperazine referred to as "Compound (41)";
(42) 1-(5-isoquinolinesulfonyl)-4-ethylpiperazine referred to as "Compound (42)";
(43) 1-(5-isoquinolinesulfonyl)-3-ethylpiperazine referred to as "Compound (43)";
(44) 1-(5-isoquinolinesulfonyl)-4-n-propylpiperazine referred to as "Compound (44)";
(45) 1-(5-isoquinolinesulfonyl)-3-isopropylpiperazine referred to as "Compound (45)";
(46) 1-(5-isoquinolinesulfonyl)-3-isobutylpiperazine referred to as "Compound (46)";
(47) 1-(5-isoquinolinesulfonyl)-4-isobutylpiperazine referred to as "Compound (47)";
(48) 1-(5-isoquinolinesulfonyl)-2,5-diethylpiperazine referred to as "Compound (48)";
(49) 1-(5-isoquinolinesulfonyl)-2-methyl-5-isobutylpiperazine referred to as "Compound (49)";
(50) 1-(5-isoquinolinesulfonyl)-2-methyl-5-benzylpiperazine referred to as "Compound (50)";
(51) 1-(5-isoquinolinesulfonyl)-4-hexylpiperazine referred to as "Compound (51)";
(52) 1-(5-isoquinolinesulfonyl)-2-phenylpiperazine referred to as "Compound (52)";
(53) 1-(5-isoquinolinesulfonyl)-3-phenylpiperazine referred to as "Compound (53)";
(54) 1-(5-isoquinolinesulfonyl)-3-benzylpiperazine referred to as "Compound (54)";
(55) 1-(5-isoquinolinesulfonyl)-4-phenylpiperazine referred to as "Compound (55)";
(56) 1-(5-isoquinolinesulfonyl)-4-benzylpiperazine referred to as "Compound (56)";
(57) 1-(5-isoquinolinesulfonyl)-4-phenethylpiperazine referred to as "Compound (57)";
(58) 1-(5-isoquinolinesulfonyl)-4-benzoylpiperazine referred to as "Compound (58)";
(59) 1-(5-isoquinolinesulfonyl)-4-cinnamylpiperazine referred to as "Compound (59)";
(60) 1-(5-isoquinolinesulfonyl)-4-cinnamoylpiperazine referred to as "Compound (60)";
(61) 1-(5-isoquinolinesulfonyl)-4-furoylpiperazine referred to as "Compound (61)";
(62) 1-(5-isoquinolinesulfonyl)-4-(2-methoxy-2-phenylethyl)piperazine referred to as "Compound (62)";
(63) 1-(5-isoquinolinesulfonyl)-4-(2-ethoxy-2-phenylethyl)piperazine referred to as "Compound (63)";
(64) 1-(5-isoquinolinesulfonyl-4-(2-isobutoxy-2-phenylethyl)piperazine referred to as "Compound (64)";
(65) N-[2-(N-methyl-N-benzylamino)ethyl]-5-isoquinolinesulfonamide referred to as "Compound (65)";
(66) N-[2-(N-ethyl-N-benzylamino)ethyl]-5-isoquinolinesulfonamide referred to as "Compound (66)";
(67) N-[2-(N-isopropyl-N-benzylamino)ethyl]-5-isoquinolinesulfonamide referred to as "Compound (67)";
(68) 1-(5-isoquinolinesulfonyl)-3,3-dimethylpiperazine referred to as "Compound (68)";
and the pharmaceutically acceptable acid addition salts thereof.

The acid addition salts of the isoquinolinesulfonyl derivatives of Formula (I) according to this invention are pharmaceutically acceptable non-toxic salts and can be prepared by conventional methods.

Suitable examples of such pharmaceutically acceptable acid addition salts include the salts of inorganic acids such as hydrochloric acid, hydrobromic acid, phosphoric acid, and sulfuric acid; and the salts of organic acids such as acetic acid, citric acid, tartaric acid, lactic acid, succinic acid, fumaric acid, maleic acid, methanesulfonic acid and p-toluenesulfonic acid.

The isoquinolinesulfonyl derivatives of Formula (I) of this invention can be prepared by reacting a 5-isoquinolinesulfonyl chloride of Formula (II) with a compound of Formula (III) in accordance with the following equation:

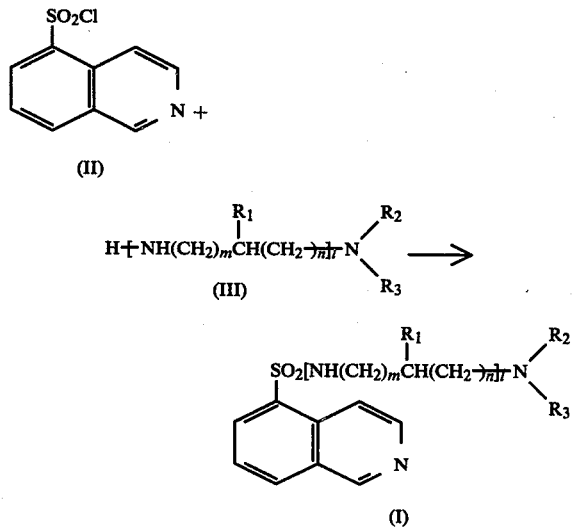

wherein l, m, n, $R_1$, $R_2$ and $R_3$ are the same as defined above.

Exemplary compounds of Formula (III) include 1,2-diaminoethane, 1,3-diaminopropane, 1,4-diaminobutane, 1,5-diaminopentane, 1,6-diaminohexane, 1,8-diaminooctane, 1,10-diaminodecane, methylamine, ethylamine, n-propylamine, isopropylamine, n-butylamine, isobutylamine, n-hexylamine, dimethylamine, diethylamine, di-n-2-(N-methyl-N-benzylamino)ethylamine, 2-(N-ethyl-N-benzylamino)ethylamine, 2-(N-isopropyl-N-benzylamino)ethylamine, butylamine, di-n-hexylamine, 3-(N,N-dimethylamino)propylamine, 3-(N,N-diethylamino)propylamine, 3-(di-n-propylamino)propylamine, 3-diisopropylamino)propylamine, 3-(di-n-butylamino)propylamine, 3-(diisobutylamino)propylamine, 3-(N-methyl-N-cyclohexylamino)propylamine, 3-(N-methyl-N-phenylamino)propylamine, 3-(N-methyl-N-benzylamino)propylamine, 3-piperidinopropylamine, 3-pyrrolidinopropylamine, 3-morpholinopropylamine, piperidine, piperazine, morpholine, pyrrolidine, 2-methylpiperazine, 1-methylpiperazine, 2-ethylpiperazine, 1-ethylpiperazine, 2-n-propylpiperazine, 1-n-propylpiperazine, 2-isopropylpiperazine, 1-isopropylpiperazine, 2-n-butylpiperazine, 1-n-butylpiperazine, 2-isobutylpiperazine, 1-isobutylpiperazine, 2-n-hexylpiperazine, 1-n-hexylpiperazine, 2,2-dimethylpiperazine, 2,3-dimethylpiperazine, 2,5-dimethylpiperazine, 2,6-dimethylpiperazine, 2,5-diethylpiperazine, 2-isobutyl-5-methylpiperazine, 2-benzyl-5-methylpiperazine, 2-phenylpiperazine, 1-phenylpiperazine, 2-benzylpiperazine, 1-benzylpiperazine, 1-phenethylpiperazine, 1-benzoylpiperazine, 1-cinnamylpiperazine, 1-cinnamoylpiperazine, 1-furoylpiperazine, 1-(2-methoxy-2-phenylethyl)piperazine, 1-(2-ethoxy-2-phenylethyl)piperazine and 1-(2-isobutoxy-2-phenylethyl)piperazine.

The reaction between the compound of Formula (II) and the compound of Formula (III) can be carried out in the presence or absence of an acid acceptor. Exemplary acid acceptors which can be employed include alkali metal compounds such as a hydroxide, bicarbonate, carbonate, hydride or an alkoxide, e.g. sodium bicarbonate, sodium carbonate, potassium carbonate, sodium hydroxide, potassium hydroxide, sodium hydride and sodium alkoxides such as sodium methoxide, sodium ethoxide and sodium tert-butoxide; and organic tertiary amines such as trimethylamine, triethylamine, 1,4-diazabicyclo[2,2,2]octane and pyridine.

In general, this reaction is carried out in the presence of a reaction medium. Exemplary reaction media which can be employed include halogenated hydrocarbons such as chloroform and dichloromethane; alcohols such as methanol, ethanol and butanol; ethers such as tetrahydrofuran and dioxane; N,N-dimethylformamide, dimethyl sulfoxide, acetonitrile and water. The reaction media may be used singly or in combination with one another.

The amount of the compound of Formula (III) which can be employed is at least 1 mol and typically ranges from 1 to about 20 mols, preferably from 1 to 10 mols per mol of the compound of Formula (II). A more preferred amount of the compound of Formula (III) ranges from 1 to 5 mols per mol of the compound of Formula (II) when the acid acceptor is present, and from 2 to 10 mols per mol of the compound of Formula (II) when the acid acceptor is absent. This amount, however, does not apply to amines having a low boiling point such as methylamine and ethylamine.

The amount of the acid acceptor employed is preferably about 0.5 to about 10 equivalents and more preferably about 1 to about 6 equivalents for each mol of the compound of Formula (III).

The reaction between the compound of Formula (II) and the compound of Formula (III) can be carried out typically at a temperature of from about −30° C. to about 150° C. and preferably from about 0° C. to about 30° C.

While this reaction can be carried out at a pressure above atmospheric, it is generally advisable to utilize atmospheric pressure.

The reaction time which can be employed is typically about 0.5 to about 48 hours and preferably about 0.5 to 20 hours at atmospheric pressure.

Also, when $R_2$ in Formula (I) is a hydrogen atom, the 5-isoquinolinesulfonyl derivatives of this invention represented by Formula (VI) can be prepared by the following equations:

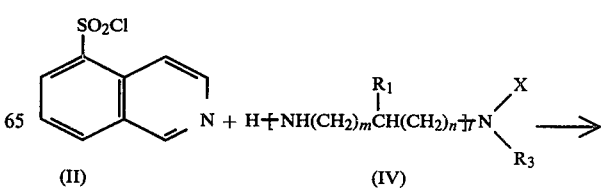

(V) Elimination of Protective Group →

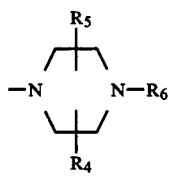

(VI)

Further, when l in Formula (I) is zero, the $$-N\begin{matrix}R_2\\R_3\end{matrix}$$

group in Formula (I) is a

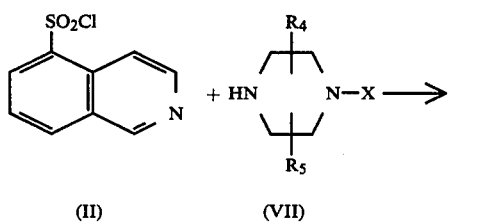

group and $R_6$ is a hydrogen atom, the 5-isoquinolinesulfonyl derivatives of this invention represented by Formula (IX) can be prepared in accordance with the following equations:

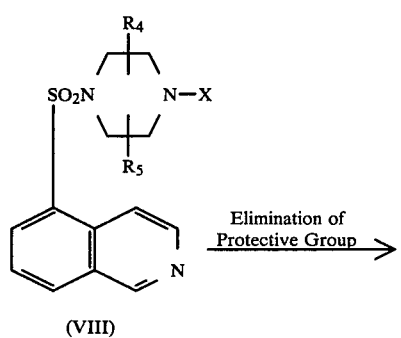

(VIII) Elimination of Protective Group →

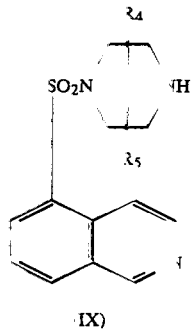

(IX)

In these Formulae, l, m, n, $R_1$, $R_3$, $R_4$ and $R_5$ are the same as defined above and X is a protective group. Exemplary protective groups represented by X which can be employed in this invention include acyl groups such as formyl, acetyl and benzoyl; arylmethyloxycarbonyl groups such as benzyloxycarbonyl; alkyloxycarbonyl groups such as tert-butoxycarbonyl; and benzyl group.

Exemplary compounds of Formulae (IV) and (VII) include $N^1$-acetyl-1,2-diaminoethane, $N^1$-acetyl-1,3-diaminopropane, $N^1$-acetyl-1,4-diaminobutane, $N^1$-acetyl-1,5-diaminopentane, $N^1$-acetyl-1,6-diaminohexane, $N^1$-acetyl-1,8-diaminooctane, $N^1$-acetyl-1,10-diaminodecane, 2-benzyloxycarbonylamino-1-methylethylamine, 1-(benzyloxycarbonylaminomethyl)propylamine, 1-(benzyloxycarbonylaminomethyl)pentylamine, 2-(benzyloxycarbonylamino)propylamine, 2-(benzyloxycarbonylamino)-3-methylbutylamine, 2-acetamidopropylamine, 2-acetamido-3-methylbutylamine, 2-acetamido-2-phenylethylamine, 2-(N-benzyl-N-methylamino)ethylamine, 2-(N-benzyl-N-ethylamino)ethylamine, 2-(N-benzyl-N-isopropylamino)ethylamine, 2-(benzyloxycarbonylamino)-1-phenylethylamine, 2-(benzyloxycarbonylamino)-2-phenylethylamine, 1-formyl-3-methylpiperazine, 1-acetyl-3-methylpiperazine, 1-benzyloxycarbonyl-3-methylpiperazine, 1-t-butyloxycarbonyl-3-methylpiperazine, 1-benzyl-3-methylpiperazine, 1-benzyloxycarbonyl-3-ethylpiperazine and 1-benzyloxycarbonyl-3-phenylpiperazine.

The reaction between the compound of Formula (II) and the compound of Formula (IV) and the reaction between the compound of Formula (II) and the compound of Formula (VII) can be carried out under the same reaction conditions as in the reaction between the compound of Formula (II) and the compound of Formula (III) to give the compound of Formula (V) and the compound of Formula (VIII), respectively. The method of obtaining the desired compound of Formula (VI) and the desired compound of Formula (IX) from the compound of Formula (V) and the compound of Formula (VIII), respectively, may vary depending upon the protective group of X selected, generally known methods can be employed in this invention. For example, when the protective group of X is an acyl group such as formyl or acetyl, the desired compounds can be obtained by hydrolysis with an acid or an alkali. When the protective group of X is a benzyl group, the desired compounds can be obtained by hydrogenation. When the protective group of X is an arylmethyloxycarbonyl group such as benzyloxycarbonyl, the desired compounds can be obtained by hydrogenation or hydrolysis with an acid. When the protective group of X is an alkyloxycarbonyl group such as tert-butoxycarbonyl, the desired products can be obtained by hydrolysis with an acid.

Furthermore, when l in Formula (I) is zero, the

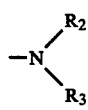

group in Formula (I) is a

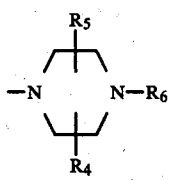

group and $R_6$ is not a hydrogen atom, the 5-isoquinolinesulfonyl derivatives of this invention represented by Formula (XII) can be prepared in accordance with the following equations:

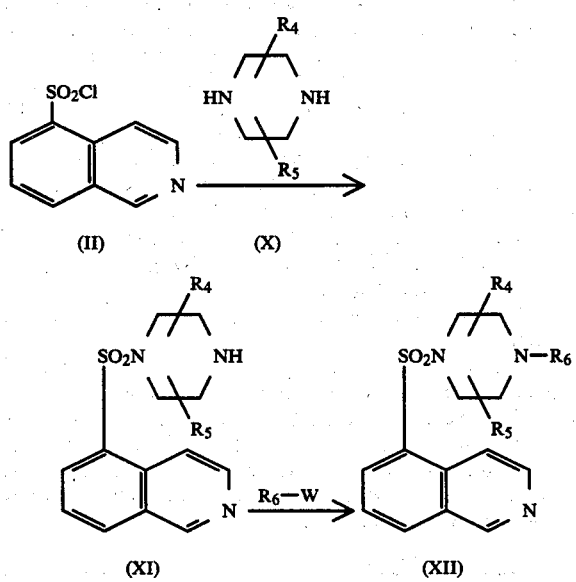

In these Formulae, $R_4$, $R_5$ and $R_6$ are the same as defined above and W is an elimination group. Exemplary elimination groups include halogen atoms such as chlorine, bromine and iodine; substituted sulfonyloxy groups such as p-toluenesulfonyloxy and methanesulfonyloxy; and sulfuric acid residue. Exemplary compounds of the formula, $R_6$-W which can be employed include dimethyl sulfate, methyl iodide, diethyl sulfate, ethyl bromide, n-propyl iodide, n-propyl bromide, isopropyl bromide, n-butyl bromide, isobutyl bromide, n-hexyl bromide, n-hexyl-p-toluenesulfonate, benzyl chloride, benzyl bromide, phenethyl bromide, benzoyl chloride, cinnamyl chloride, cinnamoyl chloride, furoyl chloride, 2-methoxy-2-phenylethyl bromide, 2-ethoxy-2-phenylethyl bromide and 2-isobutoxy-2-phenylethyl bromide.

In general, the reaction between the compound of Formula (XI) and the compound of $R_6$-W can be carried out in the presence of an acid acceptor. Exemplary acid acceptors which can be employed include the same ones as employed in the reaction between the compound of Formula (II) and the compound of Formula (III).

This reaction is, in general, carried out in the presence of a reaction medium. Exemplary reaction media which can be employed include the same one as employed in the reaction between the compound of Formula (II) and the compounds of Formula (III).

The amount of the compound of $R_6$-W which can be employed is at least 1 mol and typically ranges from 1 mol to about 20 mols, preferably from 1.2 mol to 10 mols per mol of the compound of Formula (XI).

The amount of the acid acceptor employed is preferably about 1 to about 10 equivalents and more preferably 1 to 4 equivalents for each mol of the compound of Formula (III).

The reaction between the compound of Formula (XI) and the compound of $R_6$-W can be carried out typically at a temperature of from about $-30°$ C. to about $200°$ C. and preferably from about $0°$ C. to about $100°$ C.

While this reaction may be carried out at a pressure above atmospheric or under reduced pressure, it is advisable to employ atmospheric pressure for practical purposes.

The method of separating and purifying the isoquinolinesulfonyl derivative of Formula (I) from the reaction solution comprises extracting the compound of Formula (I) with diluted hydrochloric acid, rendering the aqueous hydrochloric acid layer extracted basic, extracting the extract with a solvent such as chloroform capable of easily dissolving the extract, condensing the extract and subjecting the condensed residues to a silica gel column or an aluminum column chromatography for purification.

It has now been found that the isoquinolinesulfonyl derivatives of Formula (I) and the pharmaceutically acceptable salts have pharmacologically and biochemically interesting properties such as a relaxatory action for vascular smooth muscle and an action for increasing blood flow and are useful as a vasodilator, a hypotensor, an ameliorant of cerebral circulation, a medicine for angina pectoris and a preventive and a medicine for cardiovascular thrombosis.

The effect of the isoquinolinesulfonyl derivatives and the pharmaceutically acceptable acid addition salts of this invention on smooth muscle can be proved by suspending a mesenteric artery taken out from a rabbit in a helical form, contracting the mesenteric artery with potassium chloride and adding the isoquinolinesulfonyl derivatives or their pharmaceutically acceptable acid addition salts of this invention to the contracted mesenteric artery, resulting in the relaxation of the mesenteric artery. When, for example, 1-(5-isoquinolinesulfonyl)-4-methylpiperazine, i.e., Compound (36) was added and a complete relaxation was designated 100%, the concentration which could bring about a relaxation of 50%, i.e., ED$_{50}$ was 7.7 μM, and with 1-(5-isoquinolinesulfonyl)piperazine, i.e., Compound (35) and N-(4-aminobutyl)-5-isoquinoline sulfonamide, i.e., Compound (3), ED$_{50}$ were 0.6 μM and 11 μM, respectively.

The effect of the isoquinolinesulfonyl derivatives and the pharmaceutically acceptable acid addition salts of this invention on the vasodilatation of the femoral and vertebral arteries can be measured by anesthetizing a dog of mixed breed weighing 8 to 15 Kg by an intravenous administration of 35 mg/Kg of pentbarbital, providing an acute type probe (a product of Nippon Koden K.K., Japan) with the femoral and vertebral arteries, administering the isoquinolinesulfonyl derivatives and the pharmaceutically acceptable acid addition salts to the femoral vein through a polyethylene tube inserted into the femoral vein side chain and measuring the blood flow volume with an electromagnetic flowmeter (a product of Nippon Koden K.K., Japan, "MF-27"). Among the isoquinolinesulfonyl compounds of Formula (I) of this invention, those with l=0 and the group=the 

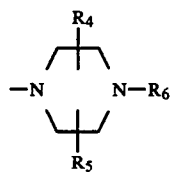

group show a high action for increasing blood flow and simultaneously a selectivity to vertebral arteries. For example, when 1 mg/Kg of 1-(5-isoquinolinesulfonyl)-piperazine, i.e., Compound (35) was intravenously administered, the increased blood flow volumes in the vertebral artery and in the femoral artery were 98% and 65%, respectively. Also the isoquinolinesulfonyl compounds of Formula (I) of this invention with l=1 and one of the $R_2$ and $R_3$ groups=a hydrogen atom show a continuing blood flow increase. With 1 mg/Kg of N-(2-aminoethyl)-5-isoquinolinesulfonamide, i.e., Compound (1), an increase in the blood flow volume in the vertebral artery was continued for at least 30 minutes.

Furthermore, when the isoquinolinesulfonyl derivatives and the pharmaceutically acceptable acid addition salts of this invention are intravenously and arterially administered for the above described purposes, any remarkable toxicity cannot be observed. For example, the acute toxicity of 1-(5-isoquinolinesulfonyl)-4-methylpiperazine, i.e., Compound (36), i.e., $LD_{50}$ was 94 mg/Kg in giving male ddY-strain mice an intravenous administration.

The following examples illustrate the present invention in more detail, but they are given for illustrative purposes only and are not to be construed as limiting the invention.

The following examples illustrate the present invention in more detail, but they are given for illustrative purposes only and are not to be construed as limiting the invention.

EXAMPLE 1

In 200 ml of chloroform was dissolved 8.8 g of 1,4-diaminobutane, and to the solution was added dropwise 100 ml of a chloroform solution containing 4.55 g of 5-isoquinolinesulfonyl chloride under cooling with ice. After the dropwise addition of the chloroform solution, the mixed solution was stirred at a temperature of 20° C. to 25° C. for two hours, and then the reaction solution was extracted with a 10% aqueous hydrochloric acid solution. The pH of the aqueous layer was adjusted to 10 with a 10% aqueous sodium hydroxide solution, and the aqueous layer was extracted with chloroform. The chloroform layer extracted was washed with water and dried with anhydrous potassium carbonate. Then the chloroform was distilled from the chloroform layer, and the residue obtained was subjected to a column chromatography [silica gel: 200 g; developing solvent: 2% methanol/chloroform (volume ratio)] to give 3.46 g of N-(4-aminobutyl)-5-isoquinolinesulfonamide, i.e., Compound (3) as an oily substance in a yield of 62%.

Mass spectrum (m/e): 279(M+) and 221

NMR spectrum (CDCl$_3$): 1.5–2.0(4H, 2×CH$_2$), 2.5–3.2(4H, 2×NCH$_2$), 2.4(2H, NH$_2$), 7.5–7.7(1H), 7.9–8.7(4H) and 9.3(1H)

IR absorption spectrum ($v_{max}{}^{cap}$ cm$^{-1}$): 1330 and 1160

The same procedures as described above were repeated using the compounds of Formula (III) as set forth in Table 1-1 under the reaction conditions as set forth in Table 1-1, and N-(ω-aminoalkyl)-5-isoquinolinesulfonamides as set forth in Table 1-2 were obtained. The results and the analytical values of these compounds are shown in Table 1-2.

TABLE 1-1

| Run No. | SO$_2$Cl (g) | Compound of Formula (III) (g) | Reaction Temperature (°C.) | Reaction Time (hour) |
|---|---|---|---|---|
| 1 | 4.55 | H$_2$N(CH$_2$)$_2$NH$_2$  12.0 | 15~20 | 2 |
| 2 | 3.41 | H$_2$N(CH$_2$)$_3$NH$_2$  11.1 | " | 4 |
| 3 | 4.55 | H$_2$N(CH$_2$)$_6$NH$_2$  11.6 | " | 5 |
| 4 | 2.28 | H$_2$N(CH$_2$)$_{10}$NH$_2$  3.62 | " | 10 |

TABLE 1-2

SO$_2$NH(CH$_2$)$_n$NH$_2$

| Run No. | Compound No. | n | Yield [g (%)] | Mass Spectrum (m/e) | IR Absorption Spectrum ($v_{SO_2}$, cm$^{-1}$) | NMR Spectrum (CDCl$_3$) |
|---|---|---|---|---|---|---|
| 1 | (1) | 2 | 3.3 (66) | 222, 221 193, 129 128 | 3400, 1610 1330, 1165 1145, 1190 | 1.5(2H, NH$_2$), 2.9(4H, 2xCH$_2$) 7.58~7.9(1H), 8.0~8.7(4H) 9.33(1H) |

TABLE 1-2-continued

Structure: 5-isoquinoline with SO$_2$NH(CH$_2$)$_n$NH$_2$

| Run No. | Compound No. | n | Yield [g (%)] | Mass Spectrum (m/e) | IR Absorption Spectrum ($\nu_{SO_2}$, cm$^{-1}$) | NMR Spectrum (CDCl$_3$) |
|---|---|---|---|---|---|---|
| 2 | (2) | 3 | 2.9 (73) | 265, 236<br>221, 143<br>128 | 1030, 830<br>3400, 1610<br>1350, 1330<br>1160, 1145<br>1090, 830 | 1.4~1.9(2H, CH$_2$)<br>2.5~3.2(4H, 2xNCH$_2$)<br>3.21(2H, NH$_2$), 7.62(1H)<br>8.0~8.8(4H), 9.33(1H) |
| 3 | (4) | 6 | 4.6 (75) | 307, 277<br>263, 243<br>221, 192<br>128 | 1590, 1320<br>1140, 1120<br>1060, 810 | 1.0~2.0(8H), 2.9~3.2(4H)<br>7.65(1H), 8.0~8.8(4H)<br>9.33(1H) |
| 4 | (5) | 10 | 2.2 (61) | 363, 320<br>292, 221<br>192, 128 | 3400, 1590<br>1350, 1330<br>1160, 1140 | 1.3(16H, 8xCH$_2$)<br>2.5~3.2(4H, 2xNCH$_2$)<br>3.3(2H, NH$_2$), 7.0(1H, NH)<br>7.6(1H), 8.1~8.8(4H)<br>9.3(1H) |

EXAMPLE 2

In 50 ml of dichloromethane was dissolved 1.73 g of 5-isoquinolinesulfonyl chloride, and to the solution were added 1.54 g of triethylamine and 8.0 g of monomethylamine hydrochloride. The mixture was stirred at a temperature of 10° C. to 15° C. for 18 hours. The reaction solution obtained was washed with water, dried with magnesium sulfate, and then the dichloromethane was distilled therefrom under reduced pressure. The residue obtained was subjected to a silica gel column chromatography (silica: 50 g; solvent: chloroform) to give 1.30 g of N-methyl-5-isoquinolinesulfonamide, i.e., Compound (25) in a yield of 77%.

Mass spectrum (m/e): 208, 148 and 128

NMR spectrum (CDCl$_3$): 2.63(3H, singlet, NCH$_3$), 3.23(1H, NH), 7.4–7.7(1H), 8.1–8.7(4H) and 9.3(1H)

IR absorption spectrum ($\nu_{max}^{cap}$ cm$^{-1}$): 3050, 2920, 1610, 1580, 1440, 1365, 1320, 1210, 1150, 1130 and 1080

The same procedures as described above were repeated using the compounds of Formula (III) as set forth in Table 2-1 under the reaction conditions as set forth in Table 2-1, and there were obtained N-ethyl-5-isoquinolinesulfonamide, i.e., Compound (26); N,N-dimethyl-5-isoquinolinesulfonamide, i.e., Compound (29); and N,N-diethyl-5-isoquinolinesulfonamide, i.e., Compound (30). The results and the analytical values of these compounds are shown in Table 2-2.

TABLE 2-1

5-isoquinolinesulfonyl chloride (SO$_2$Cl)

| Run No. | (g) | Compound of Formula (III) | (g) | N(C$_2$H$_5$)$_3$ (g) | Reaction Temperature (°C.) | Reaction Time (hour) |
|---|---|---|---|---|---|---|
| 1 | 2.28 | H$_2$N(C$_2$H$_5$).HCl | 8.2 | 10 | 15~25 | 24 |
| 2 | " | HN(CH$_3$)$_2$.HCl | 8.2 | " | " | 20 |
| 3 | 1.50 | HN(C$_2$H$_5$)$_2$.HCl | 7.2 | 6.6 | " | " |

TABLE 2-2

Structure: 5-isoquinoline-SO$_2$Y

| Run No. | Compound No. | Y | Yield [g (%)] | Mass Spectrum (m/e) | IR Absorption Spectrum ($\nu_{max}^{cap}$ cm$^{-1}$) | NMR Spectrum (CDCl$_3$) |
|---|---|---|---|---|---|---|
| 1 | (26) | —NH(C$_2$H$_5$) | 1.93 (81) | 236, 164<br>128 | 3050, 2920<br>1600, 1560<br>1440, 1360<br>1300, 1200<br>1150, 1070 | 1.15(3H, triplet)<br>2.73(2H, quartet)<br>3.33(1H, singlet, NH)<br>7.4~7.7(1H)<br>8.1~8.7(4H), 9.32(1H) |
| 2 | (29) | —N(CH$_3$)$_2$ | 1.77 (75) | 236, 191<br>143, 128 | 1600, 1470<br>1440, 1320<br>1145, 1125<br>1035, 975<br>940 | 2.85(6H, 2xCH$_3$)<br>7.5~7.9(1H)<br>8.2~8.5(4H), 9.3(1H) |
| 3 | (30) | —N(C$_2$H$_5$)$_2$ | 1.34 (77) | 264, 235<br>191, 143 | 1600, 1460<br>1360, 1150<br>1120, 1050 | 1.2~1.4(6H, 2xCH$_3$)<br>2.2~3.3(4H, 2xNCH$_2$)<br>7.5~8.6(5H), 9.3(1H) |

EXAMPLE 3

In 100 ml of methylene chloride were added 6.0 g of piperazine and 1.2 g of anhydrous potassium carbonate, and to the mixture was added dropwise 30 ml of a methylene chloride solution containing 2.0 g of 5-isoquinolinesulfonyl chloride under cooling with ice. After the dropwise addition of the methylene chloride solution, the mixed solution was stirred at a temperature of 15° C. to 25° C. for 15 hours, and then the reaction solution was washed with water, dried with anhydrous magnesium sulfate, and the methylene chloride was distilled therefrom. The residue thus obtained was subjected to a silica gel column chromatography (silica gel: 70 g; solvent: chloroform) to give 2.14 g of 1-(5-isoquinolinesulfonyl)piperazine, i.e., Compound (35) in a yield of 89%.

Mass spectrum (m/e): 277, 234, 212, 191 and 128

NMR spectrum (CDCl$_3$): 1.65(1H, N$\underline{H}$), 2.8–3.3(8H, 4×NC$\underline{H_2}$), 7.5–7.9(1H), 8.2–8.7(4H) and 9.35(1H)

IR absorption spectrum ($\nu_{max}$,$^{KBr}$ cm$^{-1}$): 3350, 1600, 1560, 1540, 1370 and 1160

EXAMPLE 4

In 100 ml of dichloromethane was dissolved 2.28 g of 5-isoquinolinesulfonyl chloride, and to the solution were added 1.38 g of anhydrous potassium carbonate and 1.46 g of n-butylamine, and the mixture thus obtained was stirred at a temperature of 20° C. to 25° C. for 12 hours. The reaction solution was washed with water, dried with anhydrous magnesium sulfate, and the dichloromethane was distilled therefrom under reduced pressure. The residue thus obtained was subjected to a silica gel column chromatography (silica gel: 70 g; solvent: chloroform) to give 1.90 g of N-n-butyl-5-isoquinolinesulfonamide, i.e., Compound (27) in a yield of 72%.

Mass spectrum (m/e): 264, 211 and 191

NMR spectrum (CDCl$_3$): 0.7–1.6(7H, C$_3$H$_7$), 2.67(2H, NC$\underline{H_2}$), 3.46(1H, N$\underline{H}$), 7.4–7.8(1$\underline{H}$), 8.1–8.6(4H) and $\overline{9.3(1H)}$ IR absorption spectrum ($\nu_{max}$,$^{cap}$ cm$^{-1}$); 3070, 2920, 1610, 1580, 1450, 1360, 1300, 1150, 1080

The same procedures as described above were repeated using the compounds of Formula (III) as set forth in Table 3-1 under the reaction conditions as set forth in Table 3-1, and there were obtained N-isobutyl-5-isoquinolinesulfonamide, i.e., Compound (28); N,N-di-n-butyl-5-isoquinolinesulfonamide, i.e., Compound (31); 1-(5-isoquinolinesulfonyl)piperazine, i.e., Compound (32); 1-(5-isoquinolinesulfonyl)pyrrolidine, i.e., Compound (33); and 1-(5-isoquinolinesulfonyl)morpholine, i.e., Compound (34). The results and the analytical values of these compounds are shown in Table 3-2.

TABLE 3-1

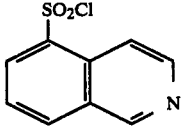

| Run No. | (g) | Compound of Formula (III) | Anhydrous Potassium Carbonate (g) | Reaction Temperature (°C.) | Reaction Time (hour) |
|---|---|---|---|---|---|
| 1 | 3.0 | H$_2$N(i-C$_4$H$_9$) | 2.4 | 2.1 | 20~25 | 5 |
| 2 | 2.5 | HN(n-C$_4$H$_9$)$_2$ | 3.6 | 2.6 | " | 8 |
| 3 | 3.0 | HN⟨piperidine⟩ | 2.8 | 2.1 | " | 2 |
| 4 | " | HN⟨pyrrolidine⟩ | 2.5 | | " | |
| 5 | " | HN⟨morpholine⟩ | 2.8 | | " | |

TABLE 3-2

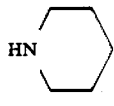

| Run No. | Compound No. | Y | Yield [g (%)] | Mass Spectrum (m/e) | IR Absorption Spectrum ($\nu_{max}^{cap}$ cm$^{-1}$) | NMR Spectrum (CDCl$_3$) |
|---|---|---|---|---|---|---|
| 1 | (28) | —NH(i-C$_4$H$_9$) | 2.37 (68) | 264, 211 191 | 3070, 2920 1610, 1580 1440, 1365 1320, 1210 1150, 1090 | 0.7~1.1(6H, 2xCH$_3$) 1.0~1.5(1H, CH) 2.55(2H, NCH$_2$) 2.62(1H, NH), 7.5~7.8(1H) 8.1~8.6(4H), 9.3(1H) |
| 2 | (31) | —N(n-C$_4$H$_9$)$_2$ | 2.43 (69) | 320, 234 191, 143 | 1600, 1470 1360, 1150 | 0.9~1.9(14H, 2xCH$_2$CH$_2$CH$_3$) 2.9~3.5(4H, 2xNCH$_2$) 7.5~8.8(5H), 9.3(1H) |

TABLE 3-2-continued

[Structure: isoquinoline with SO₂Y at position 5]

| Run No. | Compound No. | Y | Yield [g (%)] | Mass Spectrum (m/e) | IR Absorption Spectrum ($\nu_{max}^{cap}$ cm$^{-1}$) | NMR Spectrum (CDCl₃) |
|---|---|---|---|---|---|---|
| 3 | (32) | —N(piperidinyl) | 2.6 (71) | 276, 211 191, 127 | 1600, 1560 1470, 1370 1150 | 1.4~1.9(6H, 3xCH₂) 3.0~3.3(4H, 2xNCH₂) 7.6~7.9(1H), 8.2~8.8(4H) 9.4(1H) |
| 4 | (33) | —N(pyrrolidinyl) | 2.94 (85) | 262, 211 191, 127 | 1600, 1550 1470, 1350 1150 | 1.3~1.9(4H, 2xCH₂) 3.0~3.5(4H, 2xNCH₂) 7.6~7.9(1H) 8.2~8.8(4H), 9.3(1H) |
| 5 | (34) | —N(morpholinyl) O | 2.9 (79) | 278, 234 213, 191 127 | 1590, 1560 1540, 1470 1370, 1150 | 3.0~3.3(4H, 2xNCH₂) 3.6~3.8(4H, 2xOCH₂) 7.5~7.9(1H) 8.0~8.7(4H), 9.3(1H) |

EXAMPLE 5

In 50 ml of a chloroform solution containing 1.4 g of 3-dimethylaminopropylamine and 1.4 g of triethylamine was added dropwise 30 ml of a chloroform solution containing 2.6 g of 5-isoquinolinesulfonyl chloride under cooling with ice. After the dropwise addition of the chloroform solution, the mixed solution was stirred at a temperature of 2° C. to 10° C. for four hours, and the reaction mixture solution was washed with water and dried with anhydrous magnesium sulfate. After the chloroform was distilled therefrom, the residue obtained was subjected to a silica gel column chromatography (silica gel: 70 g; solvent: chloroform) to give 2.38 g of N-(3-dimethylaminopropyl)-5-isoquinolinesulfonamide, i.e., Compound (17) in a yield of 71%.

Mass spectrum (m/e): 293, 249, 235, 221 and 207

NMR spectrum (CDCl₃): 1.6(2H, CH₂), 2.0–2.6(8H, 2×NCH₃+NCH₂), 3.1(2H, NCH₂), 6.2(NH), 7.4–7.7(1H), 8.0–8.6(4H) and 9.3(1H)

IR absorption spectrum ($\nu_{max}^{cap}$ cm$^{-1}$): 2950, 2860, 2840, 1460, 1320, 1150, 1130, 830 and 760.

The same procedures as described above were repeated using the compounds of Formula (III) as set forth in Table 4-1 under the reaction conditions as set forth in Table 4-1, and there were obtained N-(3-diethylaminopropyl)-5-isoquinolinesulfonamide, e.g., Compound (18); N-(3-di-n-butylaminopropyl)-5-isoquinolinesulfonamide, i.e., Compound (19); N-(3-piperidinopropyl)-5-isoquinolinesulfonamide, i.e., Compound (20); N-(3-morpholinopropyl)-5-isoquinolinesulfonamide, i.e., Compound (21); N-[3-(N-methyl-N-cyclohexylamino)propyl]-5-isoquinolinesulfonamide, i.e., Compound (22); N-[3-(N-methyl-N-phenylamine)propyl]-5-isoquinolinesulfonamide, i.e., Compound (23); and N-[3-(N-methyl-N-benzylamino)propyl]-5-isoquinolinesulfonamide, i.e., Compound (24). The results and the analytical values of these compounds are shown in Table 4-2.

TABLE 4-1

[Structures: 5-isoquinolinesulfonyl chloride (SO₂Cl) and H₂N(CH₂)₃N(R₂)(R₃)]

| Run No. | (g) | (g) | N(C₂H₅)₃ (g) | Reaction Temperature (°C.) | Reaction Time (hour) |
|---|---|---|---|---|---|
| 1 | 1.0 | H₂N(CH₂)₃N(C₂H₅)₂ | 0.7 | 0.67 | 2~5 | 5 |
| 2 | " | H₂N(CH₂)₃N(n-C₄H₉)₂ | 1.0 | " | 5~10 | " |
| 3 | " | H₂N(CH₂)₃N(piperidinyl) | 0.8 | " | 10~20 | 12 |
| 4 | " | H₂N(CH₂)₃N(morpholinyl) | 0.8 | " | 15~25 | 18 |

TABLE 4-1-continued

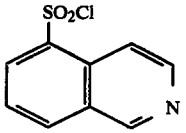

| Run No. | (g) | (g) | N(C₂H₅)₃ (g) | Reaction Temperature (°C.) | Reaction Time (hour) |
|---|---|---|---|---|---|
| 5 | 0.44 | 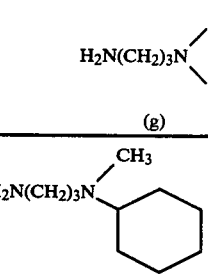 | 0.4 | 0.3 | " | " |
| 6 | " | 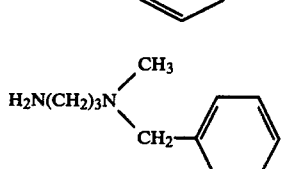 | 0.38 | " | " | " |
| 7 | 0.75 | 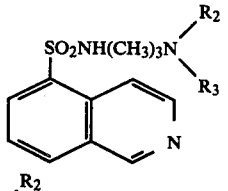 | 0.75 | 0.5 | " | " |

TABLE 4-2

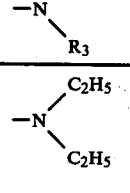

| Run No. | Compound No. | −N(R₂)(R₃) | Yield [g (%)] | Mass Spectrum (m/e) | IR Absorption Spectrum ($\nu_{max}^{cap}$, cm⁻¹) | NMR Spectrum (CDCl₃) |
|---|---|---|---|---|---|---|
| 1 | (18) | −N(C₂H₅)(C₂H₅) | 0.75 (53) | 321, 249 235, 221 207, 192 | 2950, 2850 1460, 1320 1160, 1130 | 1.1(6H, 2xCH₃) 1.5~2.0(2H, CH₂) 2.0~2.6(6H, 3xNCH₂) 3.1(2H, NCH₂), 6.8(1H, NH) 7.6(1H), 8.0~8.5(4H) 9.3(1H) |
| 2 | (19) | −N(n-C₄H₉)(n-C₄H₉) | 0.93 (56) | 377, 334 296, 248 234, 220 140 | 2960, 2870 1460, 1325 1155, 1135 | 0.8~2.0(16H, 2xCH₃ + 5xCH₂) 2.2~2.8(6H, 3xNCH₂) 3.1(2H, NCH₂), 5.4(1H, NH) 7.7(1H), 8.1~8.7(4H), 9.3(1H) |
| 3 | (20) | 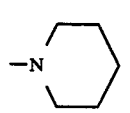 | 0.72 (49) | 332, 248 234, 220 206, 191 | 3075, 2920 2850, 2800 1320, 1160 | 1.3~2.0(8H, 4xCH₂) 2.0~2.6(6H, 3xNCH₂) 3.0(2H, NCH₂), 6.8(1H, NH) 7.6(1H), 8.1~8.7(4H), 9.3(1H) |
| 4 | (21) | 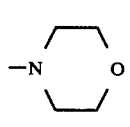 | 0.63 (43) | 334, 278 276, 248 234, 221 192, 143 128 | 2950, 2850 2820, 1320 1160, 1140 1120, 760 | 1.3~1.9(2H, CH₂) 2.0~2.7(6H, 3xNCH₂) 3.0(2H, NCH₂) 3.4~3.9(4H, 2xOCH₂) 6.5~7.1(1H, NH), 7.7(1H) 8.1~8.8(4H), 9.4(1H) |
| 5 | (22) | 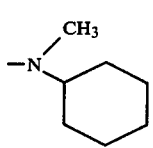 | 0.43 (62) | 361, 318 249, 221 192, 169 126 | 2930, 2850 1330, 1160 1140, 790 760 | 0.7~1.8(12H, 6xCH₂) 2.1(3H, NCH₃) 2.1~2.8(3H, NCH₂ + NCH) 2.7~3.1(2H, NCH₂) 7.1~7.5(1H, NH), 7.5(1H) 7.9~8.7(4H), 9.2(1H) |

TABLE 4-2-continued $$SO_2NH(CH_3)_3N\begin{matrix}R_2\\R_3\end{matrix}$$

(isoquinoline structure with $-N(R_2)(R_3)$ substituent)

| Run No. | Compound No. | $-N\begin{matrix}R_2\\R_3\end{matrix}$ | Yield [g (%)] | Mass Spectrum (m/e) | IR Absorption Spectrum ($\nu_{max}^{cap}$, cm$^{-1}$) | NMR Spectrum (CDCl$_3$) |
|---|---|---|---|---|---|---|
| 6 | (23) | $-N\begin{matrix}CH_3\\C_6H_5\end{matrix}$ | 0.27 (39) | 355, 163<br>134, 128<br>120 | 3050, 2900<br>2850, 1620<br>1500, 1330<br>1160, 1135<br>830, 750 | 1.5~1.9(2H), 2.7(3H, NCH$_3$)<br>2.8~3.4(4H, 2xNCH$_2$)<br>6.2(1H, NH), 6.5~6.8(3H)<br>6.9~7.3(2H), 7.6(1H)<br>8.0~8.6(4H), 9.25(1H) |
| 7 | (24) | $-N\begin{matrix}CH_3\\CH_2-C_6H_5\end{matrix}$ | 0.86 (71) | 369, 354<br>278, 221<br>177, 134<br>128, 120<br>91 | 3050, 2950<br>2850, 2800<br>1620, 1450<br>1330, 1210<br>1155, 1135 | 1.3~1.9(2H, CH$_2$), 1.95(3H, NCH$_3$)<br>2.3~2.7(2H, NCH$_2$)<br>3.0~3.3(2H, NCH$_2$)<br>3.3(2H, C$_6$H$_5$CH$_2$)<br>7.0~7.1(1H, NH)<br>7.2(5H, C$_6$H$_5$), 7.6(1H)<br>8.0~8.5(4H), 9.3(1H) |

EXAMPLE 6

In 100 ml of chloroform was dissolved 5.0 g of 1-methylpiperazine, and to the solution was added 6.9 g of anhydrous potassium carbonate. To the mixture was added dropwise 200 ml of a chloroform solution containing 1.4 g of 5-isoquinolinesulfonyl chloride under cooling with ice. After the dropwise addition of the chloroform solution, the mixed solution thus obtained was stirred for one hour under cooling with ice, and then the reaction solution was washed with 50 ml of a 5N aqueous sodium hydroxide solution and extracted twice with 50 ml of a 5N aqueous hydrochloric acid solution. The aqueous hydrochloric acid layer was rendered alkaline, extracted three times with 100 ml of chloroform, and the chloroform layer extracted was washed with water and dried with anhydrous magnesium sulfate. After the chloroform was distilled therefrom under reduced pressure, 50 ml of a 5N aqueous hydrochloric acid solution was added to the residue and the mixture was condensed to dryness under reduced pressure. The crystalline residue thus obtained was recrystallized from ethanol to give 14.9 g of 1-(5-isoquinolinesulfonyl)-4-methylpiperazine [i.e. Compound (36)] dihydrochloride in a yield of 82%.

Melting point: 215° C.

Mass spectrum (m/e): 291(M+1), 128 and 99

NMR spectrum (CDCl$_3$, δ): 2.9(3H, s, CH$_3$), 3.0–4.0(8H, m, 4×CH$_2$), 7.8–8.1(1H), 8.5–8.8(4H) and 9.6(1H, s)

IR absorption spectrum ($\nu_{max}^{KBr}$ cm$^{-1}$): 3400, 1610, 1378, 1350, 1160 and 1140.

EXAMPLE 7

In 100 ml of ethanol were added 2.77 g of 1-(5-isoquinolinesulfonyl)piperazine, i.e., Compound (35), 1.66 g of anhydrous potassium carbonate and 5.45 g of ethyl bromide, and the reaction was carried out at an external temperature of 70° C. for 24 hours. After the reaction solution was filtered, the filtrate was condensed and the residue was dissolved in 50 ml of chloroform, and the solution was extracted twice with a 2N aqueous hydrochloric acid solution. The aqueous hydrochloric acid layer was rendered alkaline, extracted twice with 50 ml of chloroform, and the chloroform layer extracted was washed with water and dried with anhydrous magnesium sulfate. After the chloroform was distilled therefrom, the residue obtained was subjected to a silica gel column chromatography (silica gel: 100 g; solvent: 2% methanol-chloroform) to give 2.26 g of 1-(5-isoquinolinesulfonyl)-4-ethylpiperazine, i.e., Compound (42) in a yield of 74%.

Melting point (the dihydrochloride recrystallized from ethanol): 221° C.

Mass spectrum (m/e): 305(M+), 290(M-15), 277, 128 and 113

NMR spectrum (CDCl$_3$, δ): 0.9(3H, t, CH$_3$), 2.2–2.8(6H, m, 3×CH$_2$), 2.9–3.4(4H, m, 2×CH$_2$), 7.5–8.9(5H, m) and 9.3(1H, s)

IR absorption spectrum ($\nu_{max}^{cap}$ cm$^{-1}$): 1610, 1350, 1340 and 1140.

EXAMPLE 8

The same procedures as in Example 7 were repeated except that 3.7 g of propyl bromide was employed instead of the 5.45 g of ethyl bromide. As a result there was obtained 1.53 g of 1-(5-isoquinolinesulfonyl)-4-propylpiperazine, i.e., Compound (44) in a yield of 48%.

Melting point (the dihydrochloride recrystallized from ethanol): 214° C.

Mass spectrum (m/e): 319(M+), 290(M-29), 127 and 88

NMR spectrum (CDCl$_3$, δ): 0.8(3H, t, CH$_3$), 1.0–1.7(2H, m, 1×CH$_2$), 2.0–2.7(6H, m, 3×NCH$_2$), 3.0–3.3(4H, m, 2×NCH$_2$), 7.5–8.7(5H, m) and 9.2(1H, s)

IR absorption spectrum ($\nu_{max}^{cap}$ cm$^{-1}$): 1607, 1350, 1260, 1165 and 1140.

EXAMPLE 9

In 30 ml of chloroform were added 1.42 g of 1-isobutylpiperazine and 2.76 g of potassium carbonate, and to the mixture was added dropwise 50 ml of a chloroform solution containing 2.28 g of 5-isoquinolinesulfonyl chloride under cooling with ice. After the dropwise addition of the chloroform solution, the mixed solution thus obtained was stirred at a temperature of 15° C. to 25° C. for two hours, and then the reaction solution was washed with 20 ml of a 1N aqueous sodium hydroxide solution and extracted twice with a 5N aqueous hydrochloric acid solution. The aqueous hydrochloric acid layer was rendered alkaline, extracted three times with 30 ml of chloroform, and the chloroform layer extracted was washed with water and dried with anhydrous magnesium sulfate. After the chloroform was distilled therefrom under reduced pressure, the residue obtained was subjected to a silica gel column chromatography (silica gel: 100 g; solvent: 2% methanol-chloroform) to give 2.60 g of 1-(5-isoquinolinesulfonyl)-4-isobutylpiperazine, i.e., Compound (47) in a yield of 78%.

Melting point (the dihydrochloride recrystallized from ethanol): 234° C.

Mass spectrum (m/e): 333(M+), 290(M-$C_3H_7$), 141 and 128

NMR spectrum ($CDCl_3$, δ): 0.8(6H, d, 2×$CH_3$), 1.2-2.0(1H, m, C$\underline{H}$), 2.0-3.3(10H, 5×NC$\underline{H}_2$), 7.6-8.8(5H) and 9.3(1$\underline{H}$, s)

IR absorption spectrum ($\nu_{max}{}^{cap}$ cm$^{-1}$): 3430, 1620, 1350, 1340, 1170 and 1145.

The same procedures as described above were repeated using the compounds of Formula (III) as set forth in Table 5-1 under the reaction conditions as set forth in Table 5-1, and there were obtained 1-(5-isoquinolinesulfonyl)-4-n-hexylpiperazine, i.e., Compound (51); 1-(5-isoquinolinesulfonyl)-phenylpiperazine, i.e., Compound (55); 1-(5-isoquinolinesulfonyl)-4-phenethylpiperazine, i.e., Compound (57); 1-(5-isoquinolinesulfonyl)-4-cinnamylpiperazine, i.e., Compound (59); and 1-(5-isoquinolinesulfonyl)-4-(2-ethoxy-4-phenylethyl)piperazine, i.e., Compound (63). The results and the analytical values of these compounds are shown in Table 5-2.

TABLE 5-1

| Run No. | (g) | (g) | $K_2CO_3$ (g) | Reaction Temperature (°C.) | Reaction Time (hour) |
|---|---|---|---|---|---|
| 1 | 2.28 | HN⟩N—n-$C_6H_{13}$ | 1.70 | 2.76 | 15~25 | 2 |
| 2 | 2.28 | HN⟩N—Ph | 1.62 | 2.76 | 15~25 | 2 |
| 3 | 2.28 | HN⟩N—$CH_2CH_2$—Ph | 1.9 | 2.76 | 15~25 | 2 |
| 4 | 2.28 | HN⟩N—CH₂CH=CH—Ph | 2.1 | 2.76 | 15~25 | 2 |
| 5 | 2.28 | HN⟩N—CH₂CH(O$C_2H_5$)—Ph | 2.34 | 2.76 | 15~25 | 2 |

TABLE 5-2

| Run No. | Compound No. | $R_6$ | Yield [g] | (%) | Mass Spectrum (m/e) | IR Absorption Spectrum ($\nu_{max}^{cap}$, cm$^{-1}$) | NMR Spectrum ($CDCl_3$) |
|---|---|---|---|---|---|---|---|
| 1 | (51) | n-$C_6H_{13}$ | 2.64 | (73) | 361, 290 169, 98 | 1620, 1460 1350, 1335 1170, 1140 | 0.6~1.8 (11H, 4 × $CH_2$ + $CH_3$) 2.2~3.7 (6H, 3 × $NCH_2$) 3.1~3.5 (4H, 2 × $NCH_2$) 7.4~8.8 (5H), 9.3 (1H) |

TABLE 5-2-continued

| Run No. | Compound No. | R6 | Yield [g] | Yield (%) | Mass Spectrum (m/e) | IR Absorption Spectrum ($\nu_{max}^{cap}$, cm$^{-1}$) | NMR Spectrum (CDCl$_3$) |
|---|---|---|---|---|---|---|---|
| 2 | (55) | —⟨phenyl⟩ | 2.44 | (69) | 353, 278<br>161 | 3400, 1605<br>1360, 1170<br>1150 | 3.8 (8H, 4 × NCH$_2$)<br>7.6 (5H, C$_6$H$_5$)<br>7.6~9.0 (5H), 9.2 (1H) |
| 3 | (57) | —CH$_2$CH$_2$—⟨phenyl⟩ | 2.44 | (64) | 290<br>(M—CH$_2$C$_6$H$_5$) | 3400, 1350<br>1330, 1155<br>950 | 2.5~4.0 (12H, 6 × CH$_2$)<br>7.3 (5H), 7.9~9.0 (5H)<br>9.8 (1H)<br>(d$^6$-dimethyl sulfoxide) |
| 4 | (59) | —CH$_2$CH=CH—⟨phenyl⟩ | 3.58 | (91) | 394, 303<br>202, 117 | 3400, 1350<br>1165, 1140<br>935 | 4.0 (8H, 4 × NCH$_2$)<br>3.9 (2H, NCH$_2$CH=)<br>6.0~6.5 (1H), 6.9 (1H)<br>7.3~7.5 (5H), 8.0~9.2 (5H)<br>9.9 (1H)<br>(CD$_3$OD) |
| 5 | (63) | —CH$_2$CH(OC$_2$H$_5$)—⟨phenyl⟩ | 3.9 | (92) | 381 (M-44)<br>290 | 3400, 1340<br>1160, 1135 | 1.2 (3H, CH$_3$)<br>2.5~4.5 (13H, 6 × CH$_2$ + CH)<br>7.2 (5H), 7.5~9.0 (5H)<br>9.3 (1H) |

EXAMPLE 10

In 150 ml of ethanol were added 2.77 g of 1-(5-isoquinolinesulfonyl)piperazine, i.e., Compound (35), 1.0 g of potassium hydroxide and 1.9 g of benzyl chloride, and the mixture was refluxed under heating for five hours. After the ethanol was removed from the reaction solution, 100 ml of chloroform was added to the resulting solution, and the solution obtained was washed with a buffer solution having a pH of 5.5 and extracted twice with 20 ml of a 2N aqueous hydrochloric acid solution. The aqueous hydrochloric acid layer was rendered alkaline, extracted twice with 50 ml of chloroform, and the chloroform layer extracted was washed with water and dried with anhydrous magnesium sulfate. After the chloroform was distilled therefrom under reduced pressure, 5 ml of a 10N aqueous hydrochloric acid solution was added to the residue and the mixture was condensed to dryness. The crystalline residue thus obtained was recrystallized from ethanol to give 2.9 g of 1-(5-isoquinolinesulfonyl)-4-benzylpiperazine [i.e., Compound (56)] dihydrochloride in a yield of 66%.

Melting point: 230° C.

Mass spectrum (m/e): 361(M+1), 290(M-C$_5$H$_{11}$), 169 and 98

NMR spectrum (d$^6$-dimethyl sulfoxide, δ): 3.0–4.0(8H, 4×NCH$_2$), 3.3(2H, s, NCH$_2$), 7.8–8.8(5H) and 9.3(1H, s)

IR absorption spectrum ($\nu_{max}^{KBr}$ cm$^{-1}$): 3550, 3450, 1360 and 1165.

EXAMPLE 11

In 50 ml of chloroform were added 2.77 g of 1-(5-isoquinolinesulfonyl)piperazine, i.e., Compound 35 and 1.54 g of anhydrous potassium carbonate, and to the mixture was added dropwise 1.70 g of benzoyl chloride under cooling with ice, and the mixture was stirred at a temperature of 15° C. to 20° C. for three hours. The reaction solution was washed with a 1N aqueous sodium hydroxide solution, then with water and dried with anhydrous magnesium sulfate. After the chloroform was distilled therefrom, the residue thus obtained was subjected to a silica gel column chromatography (silica gel: 70 g; solvent: chloroform) to give 2.7 g of 1-(5-isoquinolinesulfonyl)-4-benzoylpiperazine, i.e., Compound (58) in a yield of 71%.

Melting point (the hydrochloride): 217° C.

Mass spectrum (m/e): 381(M+), 318, 276 and 289

NMR spectrum (CDCl$_3$, δ): 3.1–3.9(8H, 4×CH$_2$), 7.2(5H), 7.5–8.5(5H) and 9.3(1H)

IR absorption spectrum ($\nu_{max}^{cap}$ cm$^{-1}$): 1690, 1370 and 1160.

The same procedures as described above were repeated using the compounds of the formula, R$_6$-W under the reaction conditions as set forth in Table 6-1, and there were obtained 1-(5-isoquinolinesulfonyl)-4-cinnamoylpiperazine, i.e., Compound (60) and 1-(5-isoquinolinesulfonyl)-4-furoylpiperazine, i.e., Compound (61). The results and analytical values of these compounds are shown in Table 6-2.

TABLE 6-1

[Structure: 5-isoquinolinesulfonyl piperazine with NH]

| Run No. | (g) | R₆—W (g) | K₂CO₃ (g) | Reaction Temperature (°C.) | Reaction Time (hour) |
|---|---|---|---|---|---|
| 1 | 2.77 | [phenyl]—CH=CHCCl(=O) 2.0 | 1.54 | 15~20 | 3 |
| 2 | 2.77 | [furyl]—COCl 1.58 | 1.54 | 15~20 | 3 |

TABLE 6-2

[Structure: 5-isoquinolinesulfonyl piperazine with N—R₆]

| Run No. | Compound No. | R₆ | Yield [g (%)] | Mass Spectrum (m/e) | IR Absorption Spectrum ($\nu_{max}^{cap}$ cm$^{-1}$) | NMR Spectrum (CDCl₃) |
|---|---|---|---|---|---|---|
| 1 | 60 | [phenyl]—CH=CH—C(=O)— | 3.26 (80) | 407, 344, 277, 215 | 3400, 1645, 1600, 1360, 1165 | 3.2~3.8(8H, 4 × CH₂) 6.7~7.5(2H, 2 × CH) 7.3(5H), 7.9~9.2(5H) 10.0(1H) |
| 2 | 61 | [furyl]—C(=O)— | 3.26 (88) | 371 | 3400, 1620, 1490, 1335, 1170, 1150 | 3.0~4.0(8H, 4 × CH₂) 6.4(1H), 6.95(1H) 7.4(1H), 7.4~8.8(5H) 9.3(1H) |

EXAMPLE 12

In 30 ml of methylene chloride were dissolved 1.75 g of 2,5-dimethylpiperazine and 1.53 g of triethylamine, and to the solution was added dropwise 20 ml of a methylene chloride solution containing 1.73 g of 5-isoquinolinesulfonyl chloride under cooling with ice. After the dropwise addition of the methylene chloride solution, the mixed solution obtained was stirred at a temperature of 5° C. to 10° C. for three hours, and then the reaction mixture solution was washed with water and dried with anhydrous magnesium sulfate. After the methylene chloride was distilled therefrom, the residue obtained was subjected to an alumina column chromatography (alumina: 50 g; solvent: chloroform) to give 1.38 g of 1-(5-isoquinolinesulfonyl)-2,5-dimethylpiperazine, Compound (40) in a yield of 59%.

Mass spectrum (m/e): 305, 277, 249, 192 and 128

NMR spectrum (CDCl₃): 0.8–1.3(6H, 2×CH₃), 1.7(1H, NH), 2.3–4.2(6H, 2×CH₂+2×CH), 7.6(1H), 8.0–8.8(4H) and 9.3(1H).

The same procedures as described above were repeated using the compounds of Formula (III) as set forth in Table 7-1 under the reaction conditions as set forth in Table 7-1, and there were obtained 1-(5-isoquinolinesulfonyl)-3-methylpiperazine, i.e., Compound (37); 1-(5-isoquinolinesulfonyl)-3,5-dimethylpiperazine, i.e., Compound (39); 1-(5-isoquinolinesulfonyl)-2,3-dimethylpiperazine, i.e., Compound (41); 1-(5-isoquinolinesulfonyl)-3-ethylpiperazine, i.e., Compound (43); 1-(5-isoquinolinesulfonyl)-3-isopropylpiperazine, i.e., Compound (45); 1-(5-isoquinolinesulfonyl)-3-isobutylpiperazine, i.e., Compound (46); 1-(5-isoquinolinesulfonyl)-2,5-diethylpiperazine, i.e., Compound (48); 1-(5-isoquinolinesulfonyl)-2-methyl-5-isobutylpiperazine, i.e., Compound (49); 1-(5-isoquinolinesulfonyl)-2-methyl-5-benzylpiperazine, i.e., Compound (50); 1-(5-isoquinolinesulfonyl)-3-phenylpiperazine, i.e, Compound (53); 1-(5-isoquinolinesulfonyl)-3-benzylpiperazine, i.e., Compound (54); and 1-(5-isoquinolinesulfonyl)-3,3-dimethylpiperazine, i.e., Compound (68). The results and the analytical values of these compounds are shown in Table 7-2.

TABLE 7-1

| Run No. | ![SO2Cl-isoquinoline] (g) | ![piperazine with R4/R5] (g) | N(C2H5)3 (g) | Reaction Temperature (°C.) | Reaction Time (hour) |
|---|---|---|---|---|---|
| 1 | 1.73 | 2-methylpiperazine — 1.52 | 1.53 | 2~10 | 2 |
| 2 | 1.73 | 2,5-dimethylpiperazine — 1.73 | 1.53 | 2~10 | 2 |
| 3 | 1.0 | 2,6-dimethylpiperazine — 1.25 | 1.1 | 15~25 | 1 |
| 4 | 1.14 | 2-ethylpiperazine — 1.14 | 1.0 | 15~25 | 10 |
| 5 | 1.14 | 2-isopropylpiperazine — 1.28 | 1.0 | 15~25 | 18 |
| 6 | 1.14 | 2-isobutylpiperazine — 1.42 | 1.0 | 15~25 | 18 |
| 7 | 1.73 | 2,5-diethylpiperazine — 2.28 | 1.53 | 15~25 | 18 |
| 8 | 1.0 | 2-methyl-5-isobutylpiperazine — 3.43 | 2.3 | 38 | 20 |
| 9 | 1.0 | 2-methyl-5-benzylpiperazine — 4.17 | 2.3 | 38 | 20 |

TABLE 7-1-continued

| Run No. | ![SO2Cl-isoquinoline] (g) | ![piperazine with R4/R5] (g) | N(C2H5)3 (g) | Reaction Temperature (°C.) | Reaction Time (hour) |
|---|---|---|---|---|---|
| 10 | 1.0 | R4 = C6H5, R5 = H (piperazine) 3.56 | 2.3 | 38 | 20 |
| 11 | 1.0 | R4 = CH2C6H5, R5 = H (piperazine) 3.90 | 2.3 | 38 | 20 |
| 12 | 1.14 | R4 = CH3, R5 = CH3 (piperazine) 1.14 | 1.0 | 15~25 | 20 |

TABLE 7-2

| Run No. | Compound No. | R4, R5 | Yield [g (%)] | Mass Spectrum (m/e) | IR Absorption Spectrum ($\nu_{max}^{cap}$, cm$^{-1}$) | NMR Spectrum (CDCl3) |
|---|---|---|---|---|---|---|
| 1 | (37) | R4 = CH3, R5 = H | 1.60 (88) | 276, 206, 162, 148 | 3300, 3000, 2950, 2850, 1610, 1560, 1480, 1360, 1330, 1160, 1140, 1070, 1040 | 0.95(3H, CH3), 1.6(1H, NH) 1.8 ~ 3.2(5H), 3.65(2H) 7.6(1H),8.1 ~ 8.7(4H) 9.3(1H) |
| 2 | (39) | R4 = CH3, R5 = CH3 (2,5) | 2.14 (92) | 305, 278, 264, 249, 192, 128, 114 | 3350, 2920, 2850, 1450, 1370, 1330, 1155, 1140 | 1.0(6H, 2xCH3), 2.1(2H) 2.5 ~ 3.3(2H), 3.6 ~ 4.0(2H) 4.3(1H, NH), 7.8(1H) 8.1 ~ 8.8(4H), 9.4(1H) |
| 3 | (41) | R4 = CH3, CH3 (gem-dimethyl), R5 = H | 1.0 (75) | 305, 277, 249, 192, 128 | 3400, 2920, 2850, 1610, 1360, 1330, 1160, 1140 | 0.9 ~ 1.3(6H, 2 × CH3) 1.6(1H,NH), 2.6 ~ 4.3(6H) 7.6(1H), 8.1 ~ 8.8(4H) 9.3(1H) |

TABLE 7-2-continued

[Structure: isoquinoline with SO₂N group bearing piperidine ring with R₄ and R₅ substituents]

| Run No. | Compound No. | R₅ (−N⟨⟩NH with R₄/R₅) | Yield [g] | (%) | Mass Spectrum (m/e) | IR Absorption Spectrum ($v_{max}^{cap}$, cm⁻¹) | NMR Spectrum (CDCl₃) |
|---|---|---|---|---|---|---|---|
| 4 | (43) | C₂H₅ on piperidine, −N⟨⟩NH | 1.07 | (70) | 305, 206 192, 128 114 | 3400, 2950 2800, 1600 1360, 1340 1160, 1140 | 1.0(3H, CH₃), 1.4(2H) 2.1(1H, NH), 1.8 ~ 3.0(5H) 3.6(2H), 7.68(1H) 8.0 ~ 8.6(4H), 9.3(1H) |
| 5 | (45) | i-C₃H₇ on piperidine | 1.02 | (64) | 319, 276 221, 128 | 3400, 1610 1480, 1370 1335, 1160 1130 | 0.7 ~ 1.3 (7H, C₃H₇), 2.1(1H, NH) 1.8 ~ 3.5 (5H), 3.7(2H) 7.6(1H), 8.1 ~ 8.8(4H) 9.3(1H) |
| 6 | (46) | i-C₄H₉ on piperidine | 1.07 | (64) | 333, 221 128 | 3350, 1600 1470, 1360 1330, 1160 1140 | 0.5 ~ 1.3(9H, C₄H₉), 2.7(1H, NH) 2.0 ~ 3.4(5H), 3.75(2H) 7.5(1H), 8.1 ~ 8.7(4H), 9.3(1H) |
| 7 | (48) | C₂H₅ and C₂H₅ on piperidine | 1.65 | (65) | 333, 265 248, 192 | 3400, 1610 1400, 1360 1340, 1160 1130 | 0.7 ~ 1.8(10H, 2 × C₂H₅), 1.7(1H) 2.3 ~ 4.3(6H), 7.6(1H) 8.0 ~ 8.7(4H), 9.3(1H) |
| 8 | (49) | CH₃ and i-C₄H₉ on piperidine | 0.88 | (58) | 347, 220 192, 128 | 3400, 1610 1450, 1360 1340, 1160 1130 | 0.7 ~ 1.8(12H, C₄H₉ + CH₃) 1.8(1h), 2.0 ~ 4.1(6H), 7.7(1H) 8.1 ~ 8.8(4H), 9.3(1H) |
| 9 | (50) | CH₃ and CH₂-phenyl on piperidine | 1.25 | (75) | 381, 219 220, 128 | 3350, 1600 1500, 1355 1340, 1160 1130 | 1.0(3H, CH₃), 1.6(1H, NH) 2.0 ~ 4.3(8H), 7.1(5H) 7.6(1H), 8.0 ~ 8.6(4H) 9.3(1H) |
| 10 | (53) | CH₂-phenyl on piperidine | 1.23 | (79) | 353, 312 278, 235 192, 167 | 3300, 1600 1510, 1360 1335, 1160 1140 | 1.6(1H), 1.8 ~ 3.2(5H) 3.65(2H), 7.2(5H) 7.6(1H), 8.1 ~ 8.7(4H) 9.3(1H) |

TABLE 7-2-continued

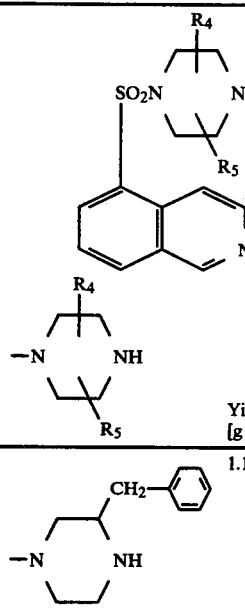

| Run No. | Compound No. | R5 | Yield [g (%)] | Mass Spectrum (m/e) | IR Absorption Spectrum ($v_{max}^{cap}$, cm$^{-1}$) | NMR Spectrum (CDCl$_3$) |
|---|---|---|---|---|---|---|
| 11 | (54) | 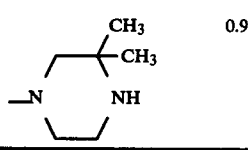 | 1.13 (70) | 367, 276 220, 148 128 | 3400, 1600 1500, 1360 1340, 1160 1140 | 1.0 ~ 1.5(2H), 1.9(1H) 1.9 ~ 3.2(5H), 3.7(2H) 7.2(5H), 7.6(1H) 8.1 ~ 8.7(4H), 9.3(1H) |
| 12 | (68) | 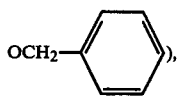 | 0.96 (63) | 305, 290 276, 191 129 | 3300, 3000 2950, 1620 1560, 1370 1160, 1140 | 1.2(6H, 2 × CH$_3$), 1.3 ~ 2.1(1H, NH) 2.6 ~ 3.4(6H, 3 × CH$_2$), 7.6(1H) 8.0 ~ 8.7(4H), 9.3(1H) |

EXAMPLE 13

In 50 ml of chloroform were dissolved 4.68 g of 1-benzyloxycarbonyl-3-methylpiperazine and 1.01 g of triethylamine, and to the solution was added dropwise 20 ml of a chloroform solution containing 4.55 g of 5-isoquinolinesulfonyl chloride, and the mixed solution was stirred at a temperature of 20° C. to 25° C. for 20 hours. The reaction solution obtained was washed with a saturated aqueous sodium hydrogencarbonate solution then with a saturated aqueous ammonium chloride solution, dried with anhydrous magnesium sulfate and concentrated to dryness under reduced pressure to 8.1 g of 1-(5-isoquinolinesulfonyl)-4-benzyloxycarbonyl-2-methylpiperazine as a yellowish white oily substance.

NMR spectrum (CDCl$_3$): 1.0(3H, d, CH$_3$), 2.5-4.3(7H), 5.0(2H, S,

OCH$_2$—C$_6$H$_5$), 7.25(5H, S, C$_6$H$_5$), 7.55(1H), 8.0-8.7(4H) and 9.2(1H)

IR absorption spectrum ($v_{max}^{cap}$ cm$^{-1}$): 1700, 1360 and 1130.

To 1.65 g of 1-(5-isoquinolinesulfonyl)-4-benzyloxycarbonyl-2-methylpiperazine as obtained above was added 5 ml of 25% hydrobromic acid-acetic acid, and the mixture was stirred at 20° C. for five hours. To the reaction solution was added 30 ml of ethyl ether, and the crystals precipitated were separated by filtration. The crystals thus obtained were dissolved in 20 ml of water and washed with chloroform. Then the pH of the aqueous layer was adjusted to 9 with a 1N aqueous sodium hydroxide solution, extracted with chloroform, and the chloroform layer was washed with water and dried with anhydrous magnesium sulfate. Then the chloroform was distilled therefrom under reduced pressure to give 1.05 g of 1-(5-isoquinolinesulfonyl)-2-methylpiperazine, i.e., Compound (38) in a yield of 93%.

Mass spectrum (m/e): 291, 277, 249, 192, 129 and 128

NMR spectrum (CDCl$_3$): 1.3(6H, d, 2×CH$_3$), 1.9(1H, NH), 2.2-3.1(4H), 3.1-4.0(2H), 4.2(1H), 7.7(1H), 8.1-8.8(4H) and 9.3(1H)

IR spectrum ($v_{max}^{cap}$ cm$^{-1}$): 3330, 2940, 2870, 2830, 1607, 1370, 1320, 1160, 1135, 990 and 760

EXAMPLE 14

In 40 ml of chloroform were dissolved 2.23 g of 2-benzyloxycarbonyl-1-methylethylamine and 1.2 g of triethylamine, and to the solution was added dropwise 20 ml of a chloroform solution containing 2.28 g of 5-isoquinolinesulfonyl chloride under cooling with ice. After the dropwise addition of the chloroform solution, the mixed solution was stirred at a temperature of 20° C. to 25° C. for two hours. The reaction solution obtained was washed with a saturated aqueous hydrogencarbonate solution, then with water, dried with anhydrous magnesium sulfate and then the chloroform was distilled therefrom under reduced pressure to give 3.55 g of N-(2-benzyloxycarbonylamino-1-methylethyl)-5-isoquinolinesulfonamide in a yield of 89%.

NMR spectrum (CDCl$_3$): 0.95(3H, CH$_3$), 2.5-4.5(3H), 5.0(2H,

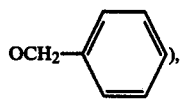

6.6(1H), 7.2(5H), 7.6(1H), 8.0–8.6(4H) and 9.3(1H)

IR absorption spectrum ($\nu_{max}{}^{cap}$ cm$^{-1}$): 3350, 1700, 1330 and 1160.

To 2.0 g of N-(2-benzyloxycarbonylamino-1-methylethyl)-5-isoquinolinesulfonamide as obtained above was added 5 ml of 25% hydrobromic acid-acetic acid, and the mixture was stirred at a temperature of 20° C. to 25° C. for 20 hours. To the reaction solution was added 30 ml of ethyl ether, and the crystals precipitated were separated by filtration. The crystals thus obtained were dissolved in 20 ml of water, washed with chloroform, rendered alkaline with a 1N sodium hydroxide solution and extracted with chloroform. The chloroform layer was washed with water, dried with anhydrous magnesium sulfate and the chloroform was distilled under reduced pressure to give 1.2 g of N-(2-amino-1-methylethyl)-5-isoquinolinesulfonamide, i.e., Compound (6) in a yield of 90%.

Mass spectrum (m/e): 265, 240, 221, 192 and 128

NMR spectrum (CDCl$_3$): 1.1(3H), 1.7(2H), 2.6(2H), 3.7(1H), 6.5(1H), 7.6(1H), 8.0–8.7(4H) and 9.3(1H)

IR absorption spectrum ($\nu_{max}{}^{cap}$ cm$^{-1}$): 3400, 2900, 1610, 1460, 1330, 1160 and 1140.

The same procedures as described above were repeated using the compounds of Formula (III) as set forth in Table 8-1 under the reaction conditions as set forth in Table 8-1 and Table 8-2, and there were obtained N-(1-aminomethylpropyl)-5-isoquinolinesulfonamide, i.e., Compound (7); N-(1-aminomethylpentyl)-5-isoquinolinesulfonamide, i.e., Compound (8); and N-(2-amino-1-phenylethyl)-5-isoquinolinesulfonamide, i.e., Compound (12). The analytical values of these compounds thus obtained are shown in Table 8-3.

TABLE 8-1

| Run No. | (g) | R$_1$ in NH$_2$CHCH$_2$NH—Z | (g) | N(C$_2$H$_5$)$_3$ (g) | Reaction Temperature (°C.) | Reaction Time (hour) | Yield [g (%)] | IR Absorption Spectrum ($\nu_{max}^{cap}$ cm$^{-1}$) |
|---|---|---|---|---|---|---|---|---|
| 1-1 | 2.28 | C$_2$H$_5$ | 2.4 | 1.2 | 20~25 | 4 | 3.5 (85) | 1710, 1330, 1160 |
| 2-1 | 2.28 | n-C$_4$H$_9$ | 2.8 | 1.2 | 20~25 | 4 | 3.1 (70) | 1710, 1340, 1160 |
| 3-1 | 2.28 | —C$_6$H$_5$ | 3.0 | 1.2 | 20~25 | 4 | 3.4 (74) | 1710, 1330, 1160 |

TABLE 8-2

| Run No. | R$_1$ | (g) | 25% HBr—CH$_3$COOH (ml) | Reaction Temperature (°C.) | Reaction Time (hour) | Product Compound No. | Yield [g (%)] |
|---|---|---|---|---|---|---|---|
| 1-2 | C$_2$H$_5$ | 1.5 | 5 | 20~25 | 12 | (7) | 0.90 (89) |
| 2-2 | n-C$_4$H$_9$ | 1.5 | 5 | 20~25 | 12 | (8) | 0.92 (88) |
| 3-2 | —C$_6$H$_5$ | 1.5 | 5 | 20~25 | 18 | (12) | 0.74 (70) |

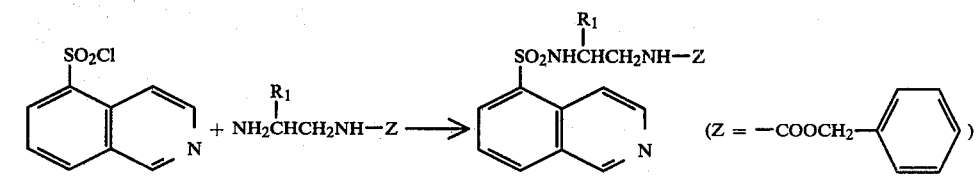

TABLE 8-3

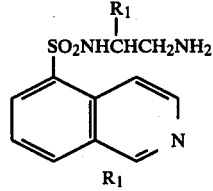

| Run No. | Compound No. | $R_1$ | Mass Spectrum (m/e) | IR Absorption Spectrum ($\nu_{max}^{cap}$, cm$^{-1}$) | NMR Spectrum (CDCl$_3$) |
|---|---|---|---|---|---|
| 1 | (7) | C$_2$H$_5$ | 279, 249, 221 192, 128 | 3400, 2900, 1460 1360, 1160, 1140 | 0.8(3H, CH$_3$), 1.0~1.7(2H) 1.9(2H, NH$_2$), 2.5~4.0(3H) 6.7(1H), 7.6~8.8(5H) 9.3(1H) |
| 2 | (8) | n-C$_4$H$_9$ | 307, 277, 221 192, 128 | 3350, 2900, 1370 1160, 1130 | 0.7~2.0(9H), 2.1(2H, NH$_2$) 2.5~3.8(3H), 7.0(1H) 7.6~8.8(5H), 9.3(1H) |
| 3 | (12) |  | 327, 297, 192 128 | 3350, 1610, 1350 1160, 1140 | 1.7(2H, NH$_2$), 2.5~4.4(3H) 6.6(1H), 7.1(5H) 7.6~8.8(5H), 9.3(1H) |

EXAMPLE 15

In 50 ml of chloroform were dissolved 2.0 g of 2-acetamidopropylamine and 2.6 g of triethylamine, and to the solution was added dropwise 50 ml of a chloroform solution containing 3.28 g of 5-isoquinolinesulfonyl chloride under cooling with ice. Then the mixed solution was stirred at a temperature of 15° C. to 25° C. for two hours, and the reaction solution was washed with water, dried with anhydrous magnesium sulfate and the chloroform was distilled therefrom under reduced pressure to give 3.67 g of N-(2-acetamidopropyl)-5-isoquinolinesulfonamide in a yield of 83%.

NMR spectrum (CDCl$_3$): 1.0(3H, d, CH$_3$), 2.2(3H, COCH$_3$), 2.6–3.8(3H), 5.5–7.0(2H), 7.6(1H), 8.0–8.7(4H) and 9.3(1H)

IR absorption spectrum ($\nu_{max}^{cap}$ cm$^{-1}$) 3300, 1670, 1365, 1150, 1130.

The reaction mixture of 3.0 g of the N-(2-acetamidopropyl)-5-isoquinolinesulfonamide as obtained above and 50 ml of 10% hydrochloric acid was stirred at a temperature of 90° C. to 100° C. for 36 hours. Then the reaction solution was washed with chloroform, rendered alkaline with 1N sodium hydroxide and extracted with chloroform. The chloroform layer was washed with water, dried with anhydrous magnesium sulfate, and the chloroform was distilled therefrom under reduced pressure. The residue thus obtained was subjected to an alumina column chromatography (alumina: 70 g; solvent: chloroform) to give 1.14 g of N-(2-aminopropyl)-5-isoquinolinesulfonamide, i.e., Compound (9) in a yield of 44%.

Mass spectrum (m/e): 265, 222, 193, 129 and 128

NMR spectrum (CDCl$_3$): 1.0(3H), 1.7(2H), 2.9–4.0(3H), 6.8(1H), 7.5(1H), 8.1–8.6(4H) and 9.3(1H)

IR absorption spectrum ($\nu_{max}^{cap}$ cm$^{-1}$): 3400, 1610, 1460, 1370, 1150 and 1130.

The same procedures as described above were repeated using the compounds of Formula (IV) as set forth in Table 9-1 under the reaction conditions as set forth in Table 9-1 and Table 9-2, and there were obtained N-(2-amino-3-methylbutyl)-5-isoquinolinesulfonamide, i.e., Compound (11) and N-(2-amino-2-phenylethyl)-5-isoquinolinesulfonamide, i.e., Compound (13). The analytical values of these compounds are shown in Table 9-3.

TABLE 9-1

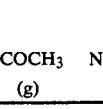

| Run No. |  (g) | $R_1$ H$_2$NCH$_2$CHNH—COCH$_3$ $R_1$ | (g) | N(C$_2$H$_5$)$_3$ (g) | Reaction Temperature (°C.) | Reaction Time (hour) | Yield g (%) | IR Absorption Spectrum ($\tau_{max}^{cap}$ cm$^{-1}$) |
|---|---|---|---|---|---|---|---|---|
| 1-1 | 2.28 | i-C$_3$H$_7$ | 2.16 | 1.6 | 15 ~ 20 | 0.5 | 2.31 (69) | 1665, 1330, 1160 |
| 2-1 | " | 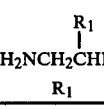 | 2.67 | " | " | 1 | 2.77 (75) | 1660, 1330, 1160 |

TABLE 9-2

Structure shown with SO₂NHCH₂CHNH—COCH₃ (with R₁) on isoquinoline.

| Run No. | R₁ | 10% HCl (g) | Reaction Temperature (ml) | Reaction Time (°C.) | Product (hour) | Compound No. | Yield [g | (%)] |
|---|---|---|---|---|---|---|---|---|
| 1-2 | i-C₃H₇ | 1.34 | 30 | 100 | 35 | (11) | 0.60 | (51) |
| 2-2 | (phenyl) | 1.11 | " | " | 30 | (13) | 0.38 | (39) |

Reaction scheme:

SO₂Cl-isoquinoline + NH₂CH₂CHNH—COCH₃ (with R₁) → SO₂NHCH₂CHNH—COCH₃ (with R₁) isoquinoline

TABLE 9-3

Structure: SO₂NHCH₂CHNH₂ (with R₁) on isoquinoline.

| Run No. | Compound No. | R₁ | Mass Spectrum (m/e) | IR Absorption Spectrum ($\nu_{max}^{cap}$ cm$^{-1}$) | NMR Spectrum (CDCl₃) |
|---|---|---|---|---|---|
| 1 | (11) | i-C₃H₇ | 221, 192, 148 128 | 3450, 1600, 1460 1330, 1160, 1140 | 0.9(6H, 2 × CH₃), 1 ~ 1.8(1H) 2.5 ~ 3.8(3H), 2.1(2H) 7.6(1H), 8.1 ~ 8.9(4H) 9.3(1H) |
| 2 | (13) | (phenyl) | 221, 192, 148 128 | 3400, 1610, 1440 1400, 1330, 1150 | 1.7(2H, NH₂), 2.7 ~ 4.0(3H) 6.8(1H), 7.2(5H), 7.6(1H) 8.0 ~ 8.8(4H), 9.3(1H) |

EXAMPLE 16

In 70 ml of methylene chloride were dissolved 3.24 g of 2-(N-methyl-N-benzylamino)ethylamine and 2.0 g of triethylamine, and to the solution was added dropwise 50 ml of a methylene chloride solution containing 3.0 g of 5-isoquinolinesulfonyl chloride under cooling with ice. After the dropwise addition of the methylene chloride solution, the mixed solution was stirred at a temperature of 15° C. to 25° C. for one hour, and then the reaction solution was washed with water and extracted with a 10% aqueous hydrochloric acid solution. The aqueous layer was washed with chloroform, rendered alkaline with a 1N aqueous sodium hydroxide solution, extracted with chloroform, and then the chloroform layer was washed with water, dried with anhydrous magnesium sulfate and the chloroform was distilled therefrom under reduced pressure. The residue thus obtained was subjected to a silica gel column chromatography (silica gel: 100 g; solvent: chloroform) to give 3.84 g of N-[2-(N-methyl-N-benzylamino)ethyl]-5-isoquinolinesulfonamide, i.e., Compound (65) in a yield of 84%.

Mass spectrum (m/e): 355, 340, 264, 221 and 128
NMR spectrum (CDCl₃): 1.9(3H, NCH₃), 2.3-2.7(2H), 3.0-3.3(2H), 3.5(2H,

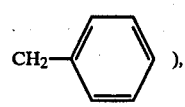
CH₂—(phenyl) ), 6.8(1H), 7.2(5H), 7.6(1H), 8.0-8.5(4H) and 9.3(1H)
IR absorption spectrum ($\nu_{max}^{cap}$ cm$^{-1}$): 3050, 2950, 1620, 1450, 1330, 1155 and 1135.

The same procedures as described above were repeated using the compound of Formula (III) as set forth in Table 10-1 under the reaction conditions as set forth in Table 10-1, and there was obtained N-[2-(N-isopropyl-N-benzylamino)ethyl]-5-isoquinolinesulfonamide, i.e., Compound (67). The analytical values of this compound are shown in Table 10-2.

TABLE 10-1

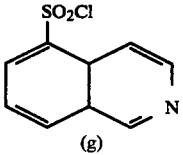

| SO₂Cl structure (g) | i-C₃H₇, H₂N(CH₂)₂N, CH₂C₆H₅ (g) | N(C₂H₅)₃ (g) | Reaction Temperature (°C.) | Reaction Time (hour) | Product Compound (67) Yield [g (%)] |
|---|---|---|---|---|---|
| 4.55 | 3.84 | 2.2 | 15 ~ 25 | 1 | 5.44 (71) |

TABLE 10-2

| Product Compound (67) | Mass Spectrum (m/e) | IR Absoprtion Spectrum ($\nu_{max}^{cap}$ cm$^{-1}$) | NMR Spectrum (CDCl₃) |
|---|---|---|---|
| 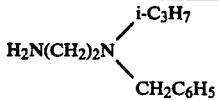 | 383, 340 221, 128 | 2950, 1610, 1450 1335, 1160, 1140 | 0.9(6H, 2 × CH₃), 2.5 ~ 2.8(3H) 3.3(2H), 3.7(2H, CH₂—⟨⟩) 6.8(1H), 7.2(5H), 7.6 ~ 8.5(5H) 9.3(1H) |

EXAMPLE 17

In 100 ml of ethanol was dissolved 2.0 g of N-[2-(N-methyl-N-benzylamino)ethyl]-5-isoquinolinesulfonamide, i.e., Compound (65) as obtained in Example 16, and to the solution was added 0.2 g of 10% palladium-carbon. Then the solution was vigorously stirred at a temperature of 20° C. to 25° C. in a hydrogen stream of 2.0 to 2.5 atm. for 5 hours. After the palladium-carbon was separated from the reaction solution by filtration, the reaction solution was concentrated to dryness to give 0.95 g of N-(2-methylaminoethyl)-5-isoquinolinesulfonamide, i.e., Compound (14) in a yield of 64%.

Mass spectrum (m/e): 265, 250, 221 and 128

NMR spectrum (CDCl₃): 1.7(1H, NH), 2.9(3H, CH₃), 2.5–3.1(2H), 3.1–3.5(2H), 7.0(1H), 7.6(1H), 8.1–8.5(4H) and 9.3(1H)

IR absorption spectrum ($\nu_{max}^{cap}$ cm$^{-1}$): 3400, 1610, 1350, 1330, 1160 and 1140.

The same procedures as described above were repeated using Compound (67) under the reaction conditions as set forth in Table 11-1, and there was obtained N-(2-isopropylaminoethyl)-5-isoquinolinesulfonamide, i.e., Compound (16). The analytical values of this compound are shown in Table 11-2.

TABLE 11-1

| Starting Material (g) | 10% Pd-C (g) | Hydrogen Pressure (atm.) | Reaction Temperature (°C.) | Reaction Time (hour) | Product Yield [g (%)] |
|---|---|---|---|---|---|
| 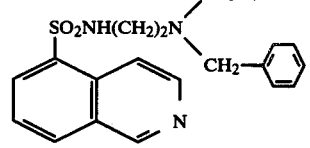 | 0.15 | 2 | 20 ~ 25 | 10 | 0.50 (44) |

TABLE 11-2

| Product Compound (16) | Mass Spectrum (m/e) | IR Absoprtion Spectrum ($\nu_{max}^{cap}$ cm$^{-1}$) | NMR Spectrum (CDCl₃) |
|---|---|---|---|
| 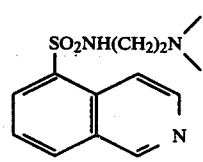 | 293, 263, 221 143, 128 | 3400, 1600, 1350, 1330 1160, 1140 | 1.0(6H, 2 × CH₃), 2.1(1H, NH) 2.5 ~ 2.9(2H), 3.0 ~ 3.5(3H) 6.8(1H), 7.6 ~ 8.8(5H), 9.3(1H) |

RELAXATION OF MESENTERIC ARTERY

After a home bred rabbit of a Japanese species weighing about 3 Kg was subjected to bloodletting, resulting in death and then to abdominal incision, the mesenteric artery was taken out, cut into helicoids of 2 mm×25 mm and suspended in a 20 ml organ bath filled with a Krebs-Henseleit solution into which a mixed gas of 95% by volume of O₂ and 5% by volume of CO₂ was introduced and one end of the artery was connected with an isometric transducer. When a load of 1.5 g was applied to the artery, the contraction and the relaxation of the artery were recorded as a weight on the transducer (a product of Nippon Koden K.K., Japan, "FD Pickup TB-912T"). The relaxation of the mesenteric artery was observed by adding the isoquinolinesulfonyl derivatives and their pharmaceutically acceptable acid addition salts of this invention to the mesenteric artery at the condition of about one half of the maximum contraction with KCl at a KCl concentration of 15-20 mM. When the complete relaxation of the mesenteric artery was designated 100%, the concentration of the isoquinolinesulfonyl derivatives and their pharmaceutically acceptable acid addition salts which brought about a relaxation of 50% is shown in Table 12.

TABLE 12

| Compound Nos. | Relaxation of Mesenteric Artery ED$_{50}$ ($\mu$M) | Compound Nos. | Relaxation of Mesenteric Artery ED$_{50}$ ($\mu$M) |
|---|---|---|---|
| (1) | 5 | (34) | 10 |
| (2) | 7 | (35) | 0.6 |
| (3) | 11 | (36) | 7.7 |
| (4) | 10 | (37) | 4.0 |
| (5) | 14 | (38) | 5.0 |
| (6) | 10 | (39) | 9.5 |
| (7) | 21 | (40) | 0.6 |
| (8) | 19 | (41) | 1.5 |
| (9) | 15 | (42) | 18 |
| (11) | 28 | (43) | 6.1 |
| (12) | 18 | (44) | 8.6 |
| (13) | 25 | (45) | 7.5 |
| (14) | 12 | (46) | 6.5 |
| (16) | 10 | (47) | 24 |
| (17) | 10 | (48) | 1.8 |
| (18) | 30 | (49) | 10 |
| (19) | 17 | (50) | 16 |
| (20) | 42 | (51) | 19 |
| (21) | 50 | (53) | 7 |
| (22) | 42 | (54) | 11 |
| (23) | 4.0 | (55) | 9 |
| (24) | 17 | (56) | 23 |
| (25) | 13 | (57) | 12 |
| (26) | 8.8 | (58) | 40 |
| (27) | 21 | (59) | 6.8 |
| (28) | 19 | (60) | 27 |
| (29) | 13 | (61) | 24 |
| (30) | 8.9 | (63) | 13 |
| (31) | 28 | (65) | 13 |
| (32) | 16 | (67) | 18 |
| (33) | 11 | | |

EFFECT ON BLOOD FLOW VOLUME OF FEMORAL AND VERTEBRAL ARTERIES OF DOG

The effect on the vasodilatation of the femoral and vertebral arteries was measured by anesthetizing a dog of mixed breed weighing 8 to 15 Kg by an intravenous administration of 35 mg/Kg of pentbarbital, providing an acute type probe (a product of Nippon Koden K.K., Japan) with the femoral and vertebral arteries, administering the 5-isoquinolinesulfonyl derivatives and their pharmaceutically acceptable acid addition salts to the femoral vein through a polyethylene tube inserted into the femoral vein side chain and measuring the blood flow volume with an electromagnetic blood flowmeter (a product of Nippon Koden K.K., Japan, "MF-27"). The results are shown in Table 13.

TABLE 13

| Compound Nos. | Amount of Intravenous Administration (mg/Kg) | Increased Blood Flow Volume in Femoral Artery (%) | Increased Blood Flow Volume in Vertebral Artery (%) |
|---|---|---|---|
| 1 | 1 | 30 | 45 |
| 3 | 1 | 33 | 36 |
| 19 | 1 | 25 | 20 |
| 25 | 1 | 38 | 29 |
| 33 | 1 | 35 | 37 |
| 35 | 1 | 69 | 98 |
| 36 | 1 | 35 | 63 |
| 37 | 1 | 65 | 90 |
| 40 | 1 | 50 | 110 |
| 46 | 1 | 32 | 55 |
| 51 | 1 | 39 | 68 |
| 59 | 1 | 25 | 49 |

ACUTE TOXICITY

The acute toxicity of the 5-isoquinolinesulfonyl derivatives and their pharmaceutically acceptable acid addition salts was measured by giving male ddY-strain mice an intravenous administration. The results are shown in Table 14.

TABLE 14

| Compound Nos. | LD$_{50}$ (mg/Kg) |
|---|---|
| 1 | 108 |
| 3 | 87 |
| 19 | 180 |
| 25 | 137 |
| 33 | 150 |
| 35 | 29 |
| 36 | 94 |
| 37 | 89 |
| 40 | 42 |
| 46 | 130 |
| 51 | 108 |
| 59 | 145 |

While the invention has been described in detail and with reference to specific embodiments thereof, it will be apparent to one skilled in the art that various changes and modifications can be made therein without departing from the spirit and scope thereof.

What is claimed is:

1. A compound of Formula (I):

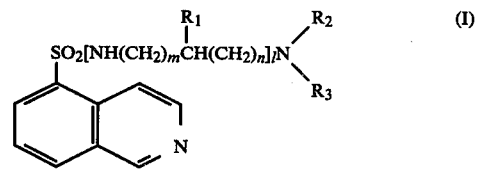

wherein
l is zero or one;
m and n each is zero or an integer of one to nine;
m+n is an integer of at least one;
R$_1$ is a hydrogen atom, a C$_{1-10}$ alkyl group, a C$_{5-6}$ cycloalkyl group or a phenyl group;
R$_2$ and R$_3$ each is a hydrogen atom, a C$_{1-10}$ alkyl group, a C$_{5-6}$ cycloalkyl group, a phenyl group or a C$_{7-10}$ phenylalkyl group; or
R$_2$ and R$_3$ are independently C$_{1-6}$ alkylene groups linked directly to form a 5- to 7-membered heterocyclic ring with the adjacent nitrogen atom;
or the pharmaceutically acceptable acid addition salt thereof.

2. The compound of claim 1 wherein l is zero; R$_2$ and R$_3$ each is a hydrogen atom, a C$_{1-8}$ alkyl group, a phenyl group or a benzyl group and when one of R$_2$ and R$_3$ is a hydrogen atom, the other is not a hydrogen atom; or $R_2$ and $R_3$ are independently $C_{1-6}$ alkylene groups linked directly to form a 5- to 7-membered heterocyclic ring together with the adjacent nitrogen atom.

3. The compound of claim 2 wherein $R_2$ is a hydrogen atom or a $C_{1-6}$ alkyl group and $R_3$ is a $C_{1-6}$ alkyl group.

4. The compound of claim 2 wherein $R_2$ and $R_3$ form together with the adjacent nitrogen atom a 1-pyrrolidinyl group or a piperidino group.

5. The compound of claim 1 wherein l is one; m and n each is zero or an integer of one to nine; m+n is an integer of one to nine; $R_1$ is a hydrogen atom, a $C_{1-6}$ alkyl or a phenyl group; $R_2$ and $R_3$ each is a hydrogen atom, a $C_{1-8}$ alkyl group, a $C_{5-6}$ cycloalkyl group, a phenyl group or a benzyl group; or $R_2$ and $R_3$ are independently $C_{1-6}$ alkylene groups linked directly to form a 5- to 7-membered heterocyclic ring together with the adjacent nitrogen atom.

6. The compound of claim 5 wherein m and n each is zero or an integer of one to nine; m+n is an integer of one to nine; and $R_1$, $R_2$ and $R_3$ are hydrogen atoms.

7. The compound of claim 5 wherein m and n each is zero or one; m+n is one; $R_1$ is a $C_{1-6}$ alkyl group or a phenyl group; and $R_2$ and $R_3$ are hydrogen atoms.

8. The compound of claim 5 wherein m and n each is zero or an integer of one to two; m+n is one or two; $R_1$ is a hydrogen atom; $R_2$ is a hydrogen atom or a $C_{1-4}$ alkyl group; and $R_3$ is a $C_{1-6}$ alkyl group, a $C_{5-6}$ cycloalkyl group, a phenyl group or a benzyl group.

9. The compound of claim 5 wherein m and n each is zero or an integer of one to two; m+n is one or two; and $R_2$ and $R_3$ form together with the adjacent nitrogen atom a piperidino group.

* * * * *

UNITED STATES PATENT AND TRADEMARK OFFICE
CERTIFICATE OF CORRECTION

PATENT NO. : 4,456,757

DATED : June 26, 1984

INVENTOR(S) : HIROYOSHI HIDAKA ET AL.

It is certified that error appears in the above-identified patent and that said Letters Patent is hereby corrected as shown below:

In the Abstract, line 7, change "1 is a zero or one;" to --$\ell$ is a zero or one;--.

In the Specification, col. 1, line 26, change "1 is a zero or one;" to --$\ell$ is a zero or one;--.

In the Specification, col. 9, line 36, change "wherein 1," to --wherein $\ell$,--.

In the Specification, col. 12, line 16, change "In these Formulae, 1," to --In these Formulae, $\ell$,--.

In the Specification, col. 13, line 3, change "Furthermore, when 1" to --Furthermore, when $\ell$--.

In the Specification, col. 15, line 33, change "with 1=1" to --with $\ell$=1--.

UNITED STATES PATENT AND TRADEMARK OFFICE
CERTIFICATE OF CORRECTION

PATENT NO. : 4,456,757

DATED : June 26, 1984

INVENTOR(S) : HIROYOSHI HIDAKA ET AL.

It is certified that error appears in the above-identified patent and that said Letters Patent is hereby corrected as shown below:

In Claim 1, at col. 50, line 52, change "1 is zero or one;" to --$\ell$ is zero or one--.

In Claim 2, at col. 50, line 65, change "wherein 1 is zero" to --wherein $\ell$ is zero--.

In Claim 5, at col. 51, line 11, change "wherein 1 is one" to --wherein $\ell$ is one--.

In claim 5, at col. 51, line 11, "wherein 1 is one" should read --wherein $\ell$ is one--.

Signed and Sealed this

Nineteenth Day of March 1985

[SEAL]

Attest:

DONALD J. QUIGG

Attesting Officer     Acting Commissioner of Patents and Trademarks